United States Patent
Giaccia et al.

(10) Patent No.: US 11,400,133 B2
(45) Date of Patent: *Aug. 2, 2022

(54) RECEPTOR-BASED ANTAGONISTS OF THE PROGRAMMED CELL DEATH 1 (PD-1) PATHWAY

(71) Applicant: The Board of Trustees of the Leland Stanford Junior University, Stanford, CA (US)

(72) Inventors: Amato J. Giaccia, Stanford, CA (US); Mihalis S. Kariolis, Stanford, CA (US); Todd A. Aguilera, Stanford, CA (US)

(73) Assignee: THE BOARD OF TRUSTEES OF THE LELAND STANFORD JUNIOR UNIVERSITY, Stanford, CA (US)

(*) Notice: Subject to any disclaimer, the term of this patent is extended or adjusted under 35 U.S.C. 154(b) by 179 days.

This patent is subject to a terminal disclaimer.

(21) Appl. No.: 16/785,332

(22) Filed: Feb. 7, 2020

(65) Prior Publication Data
US 2020/0360474 A1    Nov. 19, 2020

Related U.S. Application Data

(63) Continuation of application No. 15/723,048, filed on Oct. 2, 2017, now Pat. No. 10,588,938, which is a continuation of application No. PCT/US2016/026168, filed on Apr. 6, 2016.

(60) Provisional application No. 62/143,695, filed on Apr. 6, 2015.

(51) Int. Cl.
| | |
|---|---|
| *A61K 38/17* | (2006.01) |
| *C07K 14/705* | (2006.01) |
| *A61P 31/22* | (2006.01) |
| *A61P 31/12* | (2006.01) |
| *A61P 31/20* | (2006.01) |
| *A61P 31/14* | (2006.01) |
| *A61P 31/18* | (2006.01) |
| *A61P 31/04* | (2006.01) |
| *A61P 35/04* | (2006.01) |
| *A61P 31/10* | (2006.01) |
| *A61K 45/06* | (2006.01) |
| *A61K 38/00* | (2006.01) |

(52) U.S. Cl.
CPC .......... *A61K 38/1774* (2013.01); *A61K 45/06* (2013.01); *A61P 31/04* (2018.01); *A61P 31/10* (2018.01); *A61P 31/12* (2018.01); *A61P 31/14* (2018.01); *A61P 31/18* (2018.01); *A61P 31/20* (2018.01); *A61P 31/22* (2018.01); *A61P 35/04* (2018.01); *C07K 14/70503* (2013.01); *A61K 38/00* (2013.01)

(58) Field of Classification Search
None
See application file for complete search history.

(56) References Cited

U.S. PATENT DOCUMENTS

| | | |
|---|---|---|
| 10,588,938 B2 | 3/2020 | Giaccia et al. |
| 2012/0121634 A1 | 5/2012 | Chen et al. |
| 2012/0269859 A1 | 10/2012 | Minato et al. |
| 2013/0017199 A1 | 1/2013 | Langermann et al. |

FOREIGN PATENT DOCUMENTS

| | | |
|---|---|---|
| WO | 2014124217 A1 | 8/2014 |
| WO | 2016164428 A1 | 10/2016 |

OTHER PUBLICATIONS

Cheng, et al., "Structure and Interactions of the Human Programmed Cell Death 1 Receptor", The Journal of Biological Chemistry, vol. 288, No. 17, Apr. 26, 2013, pp. 11771-11785.
Maute, et al., "Engineering High-Affinity PD-1 Variants for Optimized Immunotherapy and Immuno-PET Imaging", Proceedings of the National Academy of Sciences, vol. 112, No. 47, Nov. 10, 2015, pp. E6506-E6514.
Onlamoon, et al., "Soluble PD-1 rescues the proliferative response of simian immunodeficiency virus-specific CD4 and CD8 T cells during chronic infection", Immunology., vol. 124, No. 2, Jun. 30, 2008, pp. 277-293.
PCT/US2016/026168, "International Search Report and Written Opinion", dated Aug. 8, 2016, 9 pages.
Tannock, "Experimental Chemotherapy," The Basic Science Of Oncology Tannock and Hill, Edition, Chapter 19, 1992, pp. 338 and 352-359.

*Primary Examiner* — Peter J Reddig
(74) *Attorney, Agent, or Firm* — Kilpatrick Townsend & Stockton LLP

(57) ABSTRACT

Provided herein are compositions and methods for alleviating cancer or infection in a subject by administering a therapeutically effective amount of a pharmaceutical composition comprising an isolated PD-1 variant polypeptide. The PD-1 variant polypeptide can inhibit the activity of PD-1 by, for example, competitive or non-competitive inhibition of the interaction between wild-type PD-1 and one or more of its ligands, PD-L1 and PD-L2.

20 Claims, 4 Drawing Sheets

Specification includes a Sequence Listing.

US 11,400,133 B2

RECEPTOR-BASED ANTAGONISTS OF THE PROGRAMMED CELL DEATH 1 (PD-1) PATHWAY

The present application is a Continuation of U.S. patent application Ser. No. 15/723,048 filed Oct. 2, 2017, now U.S. Pat. No. 10,588,938, issued Mar. 17, 2020; which is a Continuation of PCT/US2016/026168 filed Apr. 6, 2016; which claims priority to U.S. Provisional Application No. 62/143,695 filed Apr. 6, 2015, the full disclosures which are incorporated herein by reference in their entirety for all purposes.

SEQUENCE LISTING

The present application is being filed along with a Sequence Listing in electronic format. The Sequence Listing file, entitled 2020-02-07_SEQ-LIST_079445-000420US-1177156.txt, was created on Feb. 6, 2020, and is 38,989 bytes in size. The information in electronic format of the Sequence Listing is incorporated herein by reference in its entirety.

BACKGROUND OF THE INVENTION

PD-1 (programmed cell death 1) is an important immune checkpoint receptor expressed by activated T cell and B cells. It functions to mediate immunosuppression. PD-1 is expressed on activated T cells, B cells, and natural killer (NK) cells. The ligands for PD-1 are PD-L1 and PD-L2, which are expressed on many tumor cells and antigen-presenting cells, such as monocytes, dendritic cells (DC) and macrophages.

PD-1 is a member of the immunoglobulin (Ig) superfamily that contains a single Ig V-like domain in its extracellular region. The PD-1 cytoplasmic domain contains two tyrosines, with the most membrane-proximal tyrosine located within an immuno-receptor tyrosine-based inhibitory motif (ITIM). PD-1 attenuates antigen receptor signaling by recruiting cytoplasmic phosphatases via its cytoplasmic domain. Human and murine PD-1 proteins share about 60% amino acid identity with conservation of four potential N-glycosylation sites, and residues that define the Ig-V domain.

PD-1 acts to deliver a negative immune response signal when induced in T cells. Activation of PD-1 via selective binding to one of its ligands activates an inhibitory immune response that decreases T cell proliferation and/or the intensity and/or duration of a T cell response. PD-1 also regulates effector T cell activity in peripheral tissues in response to infection or tumor progression (Pardoll, *Nat Rev Cancer*, 2012, 12 (4):252-264).

Endogenous immune checkpoints, such as the PD-1 signaling pathway, that normally terminate immune responses to mitigate collateral tissue damage can be co-opted by tumors to evade immune destruction. The interaction between PD-L1 and PD-1 in cancers can decrease the number of tumor-infiltrating immune cells, and inhibit an immune response to the cancer cells. Downregulation of T cell activation and cytokine secretion upon binding to PD-1 has been observed in several human cancers (Freeman et al., *J Exp Med*, 2000, 192 (7):1027-34; Latchman et al., Nat Immunol, 2001, 2 (3):261-8). In addition, the PD-1 ligand PD-L1 is overexpressed in many cancers, including breast cancer, colon cancer, esophageal cancer, gastric cancer, glioma, leukemia, lung cancer, melanoma, multiple myeloma, ovarian cancer, pancreatic cancer, renal cell carcinoma, and urothelial cancer. It has also been shown that patients with cancer have a limited or reduced adaptive immune response due to increased PD-1/PD-L1 interactions by immune cells. This increase in activated PD-1 signaling has also been seen in patients with viral infections. For instance, hepatitis B and C viruses can induce overexpression of PD-1 ligands on hepatocytes and activate PD-1 signaling in effector T-cells. This, in turn, leads to T-cell exhaustion and immune tolerance to the viral infection (Boni et al., *J Virol*, 2007, 81:4215-4225; Golden-Mason et al., *J Immunol*, 2008, 180:3637-3641).

Current PD-1 antagonists, such as pidilizumab, pembrolizumab (Keytruda®) and nivolumab (Opdivo®) are antibodies that target PD-1 on all lymphatic cells of the body. These antibodies have nanomolar affinities to PD-1, which is weaker than the interaction between PD-1 and its ligands within the immune synapse, e.g., the interface between an antigen-presenting cell and a lymphocyte.

There is a need in the art for effective protein-based therapeutic treatment that can reverse the inhibition of adaptive immunity in patients with cancer or chronic infection. The present invention satisfies this and other needs.

BRIEF SUMMARY OF THE INVENTION

In one aspect, the present invention provides an isolated PD-1 variant polypeptide, wherein the polypeptide lacks PD-1 transmembrane and intracellular domains, and wherein the polypeptide comprises at least one amino acid modification at one or more positions selected from the group consisting of N33, F37, T45, N49, A50, T59, S87, P89, C93, R96, T98, Q99, N102, R112, N116, G124, K135, R139, A140, T145, R147, and R148 relative to the wild-type PD-1 amino acid sequence set forth in SEQ ID NO:1. In particular embodiments, the at least one amino acid modification is one or more members selected from the group consisting of N33D or N33S, F37L, T45A, N49S, A50V, T59A, 587G, P89L or P89S, C93S or C93R, R96G, T98I, Q99A or Q99R, N102S, R112G, N116D or N116S, G124S, K135R, R139G, A140V, T145A or T145I, R147K, and R148G relative to SEQ ID NO:1.

The isolated PD-1 variant polypeptide can be a soluble PD-1 variant polypeptide. In some embodiments, the polypeptide comprises the amino acid sequence set forth in SEQ ID NO:2 (i.e., amino acids 33-150 of SEQ ID NO:1) and at least one amino acid modification at one or more of the selected positions relative to SEQ ID NO:1. In other embodiments, the polypeptide comprises a fragment of SEQ ID NO:2 (e.g., a ligand binding fragment thereof) and the at least one amino acid modification.

In certain embodiments, the at least one amino acid modification comprises from about 1 to about 15 or more amino acid modifications, e.g., at least about 1, 2, 3, 4, 5, 6, 7, 8, 9, 10, 11, 12, 13, 14, 15, or more amino acid modifications at the selected positions relative to SEQ ID NO:1. In other embodiments, the at least one amino acid modification comprises from about 1 to about 15 or more amino acid modifications, e.g., at least about 1, 2, 3, 4, 5, 6, 7, 8, 9, 10, 11, 12, 13, 14, 15, or more amino acid modifications in SEQ ID NO:2 wherein the selected positions are relative SEQ ID NO:1.

In some embodiments, the polypeptide further comprises at least one amino acid modification at one or more positions selected from the group consisting of M70, N74, T76, Q88, Q91, D92, H107, R115, A125, S127, K131, and A132 relative to SEQ ID NO:1. In certain instances, the at least one amino acid modification is one or more members selected from the group consisting of M70V or M70I, N74D or N74S, T76A, Q88R, Q91R, D92A or D92G, H107R, R115G, A125V, S127F or S127L or S127V, K131R, and A132I or A132V relative to SEQ ID NO:1.

In some embodiments, the at least one amino acid modification is in a region corresponding to amino acids 87-140 of SEQ ID NO:1. The at least one amino acid modification can be at one or more positions selected from the group consisting of S87, P89, C93, N116, G124, S127, A132, and A140 relative to the wild-type PD-1 amino acid sequence set forth in SEQ ID NO:1. In certain instances, the at least one amino acid modification is one or more members selected from the group consisting of S87G, P89L or P89S, C93S or C93R, N116D or N116S, G124S, S127F or S127L or S127V, A132I or A132V, and A140V relative to SEQ ID NO:1.

In other embodiments, the at least one amino acid modification is in a region corresponding to amino acids 130-140 of SEQ ID NO:1. The at least one amino acid modification can be at one or more positions selected from the group consisting of K135, R139, and A140 relative to SEQ ID NO:1. In certain instances, the at least one amino acid modification is one or more members selected from the group consisting of K135R, R139G, and A140V relative to SEQ ID NO:1.

In some embodiments, any one of the PD-1 variant polypeptides described herein can comprise at least the amino acid modifications at positions S87, P89, C93, N116, G124, S127, A132, and A140 relative to SEQ ID NO:1. The amino acid modifications can be S87G, P89L or P89S, C93S or C93R, N116D or N116S, G124S, S127F or S127L or S127V, A132I of A132V, and A140V relative to SEQ ID NO:1.

In particular embodiments, the polypeptide comprises the amino acid sequence set forth in any one of SEQ ID NOS:3-29.

In some embodiments, the at least one amino acid modification increases the binding affinity of the polypeptide to a PD-1 ligand. The PD-1 variant polypeptide can have a binding affinity of less than about $1 \times 10^{-8}$ M for a PD-1 ligand. Alternatively, the PD-1 variant polypeptide can have a binding affinity for a PD-1 ligand that is at least about 10-fold stronger than that of the wild-type PD-1 polypeptide, e.g., outside of the context of the immune synapse. In some embodiments, the variant polypeptide inhibits or prevents binding between the wild-type PD-1 polypeptide and a PD-1 ligand in vivo or in vitro. In some instances, the PD-1 ligand is PD-L1 and/or PD-L2.

In another aspect, the present invention provides a nucleic acid comprising a nucleotide sequence encoding one or more of the polypeptides described herein.

In yet another aspect, the present invention provides a pharmaceutical composition comprising a therapeutically effective amount of one or more polypeptides described herein or a pharmaceutically acceptable salt thereof. In some embodiments, the pharmaceutical composition further comprises a pharmaceutically acceptable carrier. In other embodiments, the pharmaceutical composition further comprises a cytotoxic agent.

In still yet another aspect, the present invention provides a method of treating, reducing or preventing metastasis or invasion of a tumor in a subject with cancer, the method comprising administering to the subject an effective dose of one or more polypeptides described herein. In some embodiments, the cancer is selected from the group consisting of melanoma, glioma, lymphoma, myeloma, head and neck cancer, esophageal cancer, kidney cancer, lung cancer, breast cancer, liver cancer, colorectal cancer, gallbladder cancer, gastric cancer, pancreatic cancer, prostate cancer, cervical cancer, uterine cancer, ovarian cancer, testicular cancer, and any other solid tumor cancer. The effective dose of the one or more polypeptides can inhibit, reduce, or modulate signal transduction mediated through the wild-type PD-1 polypeptide in the subject with cancer. In some cases, the effective dose of the one or more polypeptides can increase a T cell response in the subject with cancer either alone or in combination with another cancer therapy, e.g., chemotherapy or radiotherapy.

In a further aspect, the present invention provides a method of treating a subject with an infection, the method comprising administering to the subject an effective dose of one or more polypeptides described herein. In some embodiments, the infection is a fungal infection, bacterial infection or viral infection. In some embodiments, the viral infection is selected from the group consisting of a hepatitis B virus infection, hepatitis C virus infection, human papilloma virus infection, human immunodeficiency virus (HIV) infection, human T-lymphotrophic virus (HTLV) infection, Epstein-Barr virus infection, herpes virus infection, cytomegalovirus infection, and any other chronic viral infection. The effective dose of the one or more polypeptides can inhibit, reduce, or modulate signal transduction mediated by the wild-type PD-1 polypeptide in the subject with the infection. In some cases, the effective dose of the one or more polypeptides can increase a T cell response in the subject with the infection.

Other objects, features, and advantages of the present invention will be apparent to one of skill in the art from the following detailed description and figures.

DETAILED DESCRIPTION OF THE INVENTION

I. Introduction

Figure 1:
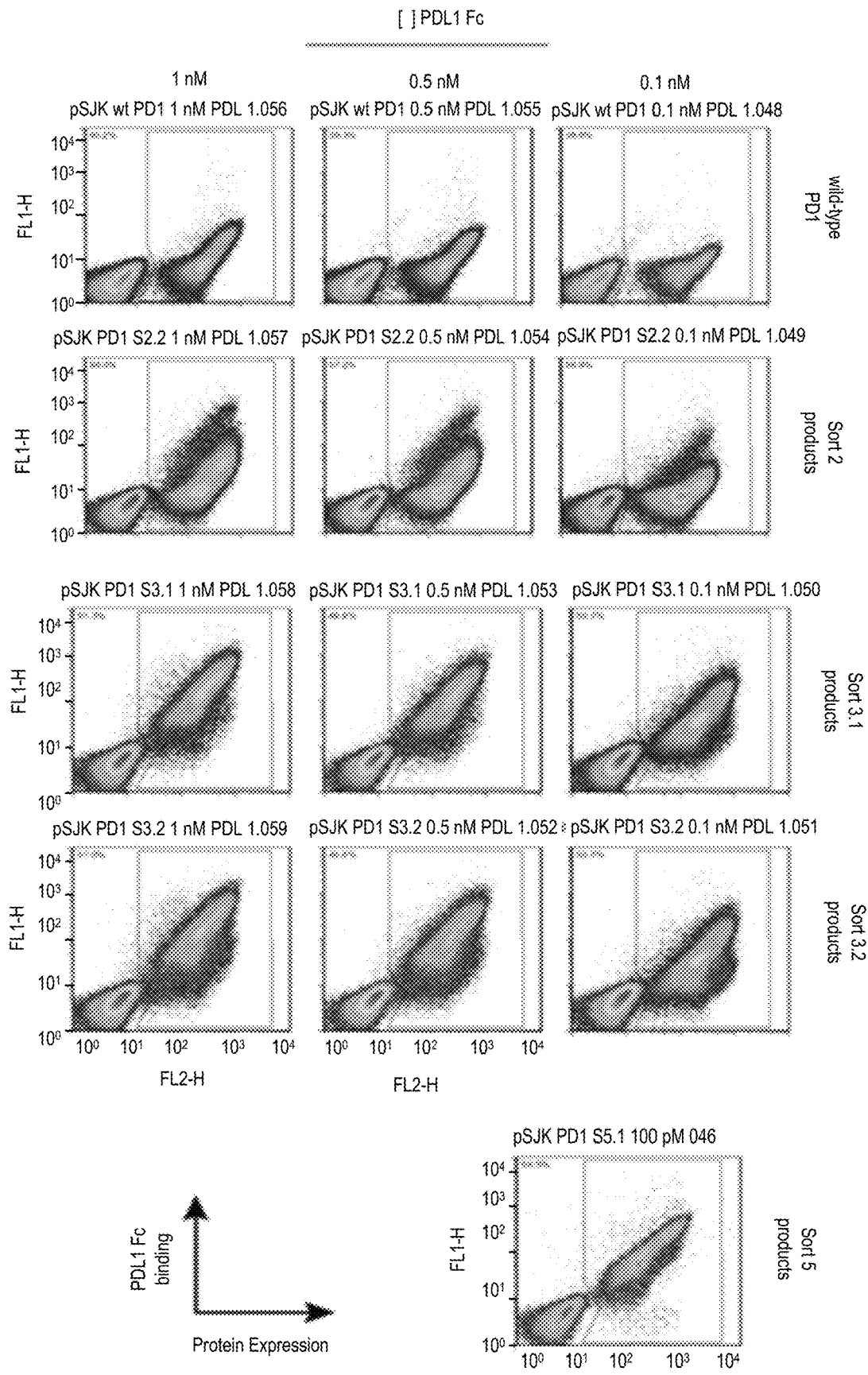
FIG. 1 shows that the engineered PD-1 variants identified in the first generation screen have increased binding to PD-L1 compared to the wild-type PD-1 receptor. After five rounds of sorting, the library of PD-1 variants was significantly enriched for variants that possessed improved binding to PD-L1 with respect to wild-type. Flow cytometry was used to measure binding of PD-L1-Fc to yeast-displayed wild-type PD-1 or pooled library sort products. The amount of binding to PD-L1 is displayed on the y-axis and expression on the cell surface of wild-type PD-1 or variants thereof is presented on the x-axis. The data shows that binding of the PD-1 variant to PD-L1 was enriched compared to wild-type over several rounds of equilibrium binding sorts.

The isolated PD-1 variant polypeptides described herein can bind to and block/antagonize PD-1 ligands, i.e., PD-L1 and/or PD-L2. The PD-1 variants can act as a competitive antagonist of PD-L1 and/or PD-L2, block the immune checkpoint PD-1 pathway, and prevent signal transduction via the PD-1 receptor. The compositions and methods provided herein block T cell inhibitory signals, and lead to immune mediated antitumor activity alone or in combination with chemotherapy, radiotherapy or anticancer drug treatment. Also, the compositions and methods can activate, enhance or increase an immune response in a subject suffering from an infection, e.g., a chronic infection. The present invention provides compositions and methods for stimulating a T cell response, such as stimulating T cell proliferation, increasing T cell activation, and/or reducing T cell inhibitory signals in patients with cancer or an infection.

II. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "isolated" refers to a molecule that is substantially free of its natural environment. For instance, an isolated protein is substantially free of cellular material or other proteins from the cell or tissue source from which it is derived. The term "isolated" also refers to preparations where the isolated protein is sufficiently pure to be administered as a pharmaceutical composition, or at least about 70-80%, 80-90%, or 90-95% (w/w) pure, or at least about 95%, 96%, 97%, 98%, 99%, or 100% (w/w) pure.

The term "PD-1 variant polypeptide" includes a variant of the wild-type programmed cell death 1 (PD-1) polypeptide containing the extracellular domain or a fragment or truncated version thereof, but not the transmembrane domain or the cytoplasmic (intracellular) domain of PD-1. The PD-1 variant polypeptides is capable of binding to a PD-1 ligand, e.g., with increased binding affinity compared to wild-type, full-length PD-1.

The terms "peptide," "polypeptide" and "protein" are used interchangeably to refer to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

The term "ligand" refers to a biomolecule that is able to bind to and form a complex with a second biomolecule such as a receptor present on the surface of target cells to serve a biological purpose. A ligand is generally an effector molecule that binds to a site on a target protein, e.g., by intermolecular forces such as ionic bonds, hydrogen bonds, hydrophobic interactions, dipole-dipole bonds, or Van der Waals forces. The PD-1 variant polypeptide of the invention can bind to and form a complex with a PD-1 ligand such as programmed cell death 1 ligand 1 (PD-L1, alternatively B7-H1) and/or programmed cell death 1 ligand 2 (PD-L2, alternatively B7-DC).

The term "receptor" refers to a biomolecule present on the surface of a target cell that is able to bind to and form a complex with a second biomolecule such as a ligand. A receptor generally activates a specific signal transduction pathway.

The term "binding affinity" refers to the ability of a ligand or variant thereof to form coordinated bonds with a protein, e.g., a receptor or a variant thereof. The binding affinity between a ligand and protein can be represented by an equilibrium dissociation constant ($K_D$), a ratio of $k_{off}/k_{on}$ between the ligand and the protein (e.g., receptor or a variant thereof). $K_D$ and binding affinity are inversely related. For instance, the $K_D$ value relates the concentration of the PD-1 variant needed to bind to a PD-1 ligand and a lower $K_D$ value (lower PD-1 variant concentration) corresponds to a higher binding affinity for the PD-1 ligand. A high binding affinity corresponds to a greater intermolecular force between the ligand and the protein. A low binding affinity corresponds to a lower intermolecular force between the ligand and the protein.

The term "variant" when as used in the context of a polypeptide refers to a polypeptide containing at least one amino acid alteration or modification as compared to the amino acid sequence of the corresponding wild-type polypeptide.

The term "amino acid" includes naturally-occurring α-amino acids and their stereoisomers, as well as unnatural (non-naturally occurring) amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an a carbon that is bound to a hydrogen, a carboxyl group, an amino group, but have modified R (i.e., side-chain) groups.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins, 1993).

The term "amino acid modification" or "amino acid alteration" refers to a substitution, a deletion, or an insertion of one or more amino acids.

The term "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. Non-limiting examples of cancer include any form of cancer, including but not limited to solid tumor cancers (e.g., lung, prostate, breast, bladder, colon, ovarian, pancreas, kidney, liver, glioblastoma, medulloblastoma, leiomyosarcoma, head and neck squamous cell carcinomas, melanomas, neuroendocrine; etc.) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors.

The term "metastasis" or "invasion" in the context of a tumor refers the growth of a secondary tumor or malignancy at a different site than the primary site of the cancer.

The term "infection" refers to the invasion of an infectious agent that is not normally present within the body. Non-limiting examples of infectious agents include, but are not limited to bacteria, viruses, protozoans, and fungi. Infectious diseases are disorders caused by infectious agents. Some infectious agents cause no recognizable symptoms or disease under certain conditions, but have the potential to cause symptoms or disease under changed conditions. The methods described herein can be used in the treatment of chronic pathogen infections, for example including but not limited to viral infections, e.g., retrovirus, lentivirus, hepadna virus, herpes viruses, pox viruses, human papilloma viruses, etc.; intracellular bacterial infections, e.g., *Mycobacterium, Chlamydophila, Ehrlichia, Rickettsia, Brucella, Legionella, Francisella, Listeria, Coxiella, Neisseria, Salmonella, Yersinia* sp, *Helicobacter pylori*, etc.; and intracellular protozoan pathogens, e.g., *Plasmodium* sp, *Trypanosoma* sp., *Giardia* sp., *Toxoplasma* sp., *Leishmania* sp., etc.

The term "immune response" refers to the action of a cell of the body's immune system (e.g., T lymphocytes, B lymphocytes, natural killer (NK) cells, macrophages, eosinophils, mast cells, dendritic cells and neutrophils) and a soluble macromolecule produced by any of these cells or the liver (including antibodies, cytokines, and complement) that results in selective targeting, binding to, damage to, destruction of, and/or elimination of invading pathogens, cells or tissues infected with pathogens, or cancerous or other abnormal cells in the body.

A "signal transduction," "signal transduction pathway" or "signaling pathway" refers to the biochemical relationship between a variety of signal transduction molecules that play a role in the transmission of a signal from one portion of a cell to another portion of the cell. A "cell surface receptor" includes, for example, molecules and complexes of molecules that are located on the surface of a cell and are capable of receiving a signal and transmitting such a signal across the plasma membrane of a cell. An example of a cell surface receptor of the present invention is the PD-1 receptor, which is located on the surface of activated B cells, activated T cells and myeloid cells, and transmits a signal that results in a decrease in tumor-infiltrating lymphocytes and a decrease in T cell proliferation. An "inhibitor" or "antagonist" of a signaling pathway refers to a compound, molecule or agent that antagonizes or reduces the initiation or transmission of a signal by any component of the signaling pathway, such as a receptor or its ligand.

The term "therapeutically effective amount" refers to the amount of a PD-1 variant polypeptide of the invention that is capable of achieving a therapeutic effect in a subject in need thereof. For example, a therapeutically effective amount of a PD-1 variant polypeptide of the invention can be the amount that is capable of preventing or relieving one or more symptoms associated with a disease or disorder. One skilled in the art will appreciate that the PD-1 variant polypeptides of the invention can be co-administered with other therapeutic agents such as anticancer, antiviral, antibiotic, and/or antifungal agents.

As used herein, the term "treating" refers to any indicia of success in the treatment of amelioration of a pathology or condition, including any objective or subjective parameter such as abatement, remission, diminishing of symptoms or making the pathology or condition more tolerable to the patient, slowing in the rate of degeneration or decline, making the final point of degeneration less debilitating, or improving a patient's physical or mental well-being. The treatment or amelioration of symptoms can be based on objective or subjective parameters, including the results of a physical examination, histopathological examination (e.g., analysis of biopsied tissue), laboratory analysis of urine, saliva, tissue sample, serum, plasma, or blood, or imaging.

As used herein, the term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a PD-1 variant polypeptide of the invention for preventing or relieving one or more symptoms associated with a disease or disorder such as cancer or an infection (e.g., microbial infection). By "co-administer" it is meant that a PD-1 variant polypeptide of the invention is administered at the same time, just prior to, or just after the administration of a second drug (e.g., anticancer agent, antiviral agent, antibiotic, antifungal agent, etc.).

The term "subject" or "patient" typically refers to humans, but can also include other animals such as, e.g., other primates, rodents, canines, felines, equines, ovines, porcines, and the like.

The term "pharmaceutical" composition is used synonymously with physiologically acceptable and pharmacologically acceptable. A pharmaceutical composition will generally comprise agents for buffering and preservation in storage, and can include buffers and carriers for appropriate delivery, depending on the route of administration.

The term "pharmaceutically acceptable salt" refers to a salt that is pharmaceutically acceptable and has the desired pharmacokinetic properties. By pharmaceutically acceptable salts is meant those salts which are suitable for use in contact with the tissues of a subject or patient without undue toxicity, irritation, allergic response and the like, and are commensurate with a reasonable benefit/risk ratio. Pharmaceutically acceptable salts are described for example, in Berge et al., *J. Pharmaceutical Sciences*, 1977, 66: 1. Particularly suitable salts include acid addition salts formed with inorganic acids (e.g., hydrochloride and hydrobromic acids) and organic acids (e.g., acetic acid, citric acid, maleic acid, and the alkane- and arene-sulfonic acids such as methanesulfonic acid and benezenesulfonic acid).

The term "pharmaceutically acceptable carrier" refers to a carrier or a diluent that does not cause significant irritation to an organism and does not abrogate the biological activity and properties of the administered polypeptide.

III. Detailed Description of the Embodiments

The present invention provides, inter alia, PD-1 polypeptide variants comprising an N-terminal and a C-terminal truncation of the full-length PD-1 receptor polypeptide. The PD-1 variants including soluble PD-1 variants are particularly useful for treating a disease or disorder in which the adaptive immune system is suppressed or an increase in the magnitude or level of immune response is needed. In some embodiments, a PD-1 variant can be used to treat cancer or chronic viral infection. In other embodiments, the PD-1 antagonists described herein can be used as adjuvant therapy for the treatment of cancer or infection.

A. PD-1 Variant Polypeptides

In certain aspects, the present invention provides isolated PD-1 variant polypeptides that have a binding affinity to PD-L1 and/or PD-L2 that is substantially equal to or higher than the binding affinity of a wild-type PD-1 polypeptide. In some embodiments, the PD-1 variant polypeptides are utilized as therapeutic agents.

Programmed cell death 1 receptor (PD-1) is an inhibitory cell surface receptor involved in controlling T-cell function during immunity and tolerance. Upon binding to its ligand, e.g., PD-L1 or PD-L2, PD-1 inhibits T-cell effector functions. The structure of PD-1 is of a single-pass type 1 membrane protein. PD-1 is encoded by the programmed cell death 1 receptor gene (Entrez GeneID: 5133). The human PD-1 mRNA (coding) sequence is set forth in, e.g., Genbank Accession No. NM_005018. The human PD-1 polypeptide sequence is set forth in, e.g., Genbank Accession No. NP_005009 or UniProt No. Q15116. PD-1 is also known as programmed cell death 1, PDCD1, PD1, CD279, SLEB2, hPD-1, and hSLE-1. The wild-type human PD-1 polypeptide is 288 amino acids (SEQ ID NO:1); the signal peptide is from residues 1 to 20 of SEQ ID NO:1, the extracellular domain is from residues 21 to 170 of SEQ ID NO:1, the transmembrane domain is from residues 171 to 191 of SEQ ID NO:1, and the intracellular domain is from residues 192 to 288 of SEQ ID NO:1.

The PD-1 variant polypeptides of the invention are polypeptides or fragments thereof that decrease, block, inhibit, abrogate and/or interfere with signal transduction resulting from the interaction of wild-type PD-1 and one or more of its binding partners, e.g., PD-L1 and/or PD-L2. In some embodiments, the PD-1 variant polypeptides inhibit or prevent the binding of wild-type PD-1 to PD-L1 and/or PD-L2. The PD-1 variant polypeptides can act as an antagonist, e.g., a competitive antagonist and reduce the negative inhibitory signal mediated by the PD-1 signaling pathway in cells including immune cells, e.g., T cells.

In some embodiments, the PD-1 variant polypeptides of the invention are antagonists the bind to and block a PD-1 ligand (e.g., PD-L1 and/or PD-L2) and thereby interfere with or inhibit the binding of the ligand to its receptor PD-1. The antagonists can enhance an immune response by inhibiting the signal transduction pathway mediated by PD-1 via reducing the amount of ligand available to bind the PD-1 receptor. As such, a more robust immune response can be produced by the subject.

In certain embodiments, the PD-1 variant includes a portion or fragment of the PD-1 polypeptide that is sufficient to bind a PD-L1 and/or PD-L2 at a recognizable affinity, e.g., high affinity, which normally lies between the signal sequence and the extracellular domain, i.e., generally from about residues 1-170 of SEQ ID NO:1, but which may comprise or consist essentially of a truncated version or fragments thereof of from about residue 1, 5, 10, 15, 20, 25, 30, 33, 35, 40, 45, or 50 to about residue 130, 135, 140, 145, 150, 155, 160, 165, or 170 of SEQ ID NO:1, e.g., residues 33-150 (SEQ ID NO:2).

In some embodiments, the PD-1 variant polypeptide of the invention is a truncated form of the wild-type full-length PD-1 polypeptide sequence that spans from about residue 21 to about residue 170, about residue 25 to about residue 170, about residue 30 to about residue 170, about residue 33 to about residue 170, about residue 35 to about residue 170, about residue 40 to about residue 170, about residue 45 to about residue 170, about residue 50 to about residue 170, about residue 21 to about residue 160, about residue 25 to about residue 160, about residue 30 to about residue 160, about residue 33 to about residue 160, about residue 35 to about residue 160, about residue 40 to about residue 160, about residue 45 to about residue 160, about residue 50 to about residue 160, about residue 21 to about residue 150, about residue 25 to about residue 150, about residue 30 to about residue 150, about residue 33 to about residue 150, about residue 35 to about residue 150, about residue 40 to about residue 150, about residue 45 to about residue 150, about residue 50 to about residue 150, about residue 21 to about residue 140, about residue 25 to about residue 140, about residue 30 to about residue 140, about residue 33 to about residue 140, about residue 35 to about residue 140, about residue 40 to about residue 140, about residue 45 to about residue 140, or about residue 50 to about residue 140 of SEQ ID NO:1. In some instances, the PD-1 variant polypeptide has 1 or more, e.g., at least 1, 2, 3, 4, 5, 6, 7, 8, 9, 10, 11, 12, 13, 14, 15 or more amino acid modifications across the length of the polypeptide.

In some embodiments, the PD-1 variant polypeptide can have at least 1, e.g., 1, 2, 3, 4, 5, 6, 7, 8, 9, 10, 11, 12, 13, 14, 15 or more amino acid substitutions located between about residue 21 to about residue 170, about residue 25 to about residue 170, about residue 30 to about residue 170, about residue 33 to about residue 170, about residue 35 to about residue 170, about residue 40 to about residue 170, about residue 45 to about residue 170, about residue 50 to about residue 170, about residue 21 to about residue 30, about residue 30 to about residue 40, about residue 40 to about residue 50, about residue 50 to about residue 60, about residue 60 to about residue 70, about residue 70 to about residue 80, about residue 80 to about residue 90, about residue 90 to about residue 100, about residue 100 to about residue 110, about residue 110 to about residue 120, about residue 120 to about residue 130, about residue 130 to about residue 140, about residue 140 to about residue 150, about residue 150 to about residue 160, or about residue 160 to about residue 170 of SEQ ID NO:1.

In some embodiments, the PD-1 variant polypeptide of the invention comprises or consists of the amino acid sequence of SEQ ID NO:2 or a fragment thereof (e.g., a fragment with ligand binding affinity) and at least 1 or more amino acid modifications (e.g., substitutions, deletions, and/or insertions), e.g., 1, 2, 3, 4, 5, 6, 7, 8, 9, 10, 11, 12, 13, 14, 15 or more amino acid modifications. The amino acid modifications can be in positions corresponding to residues 33, 37, 45, 49, 50, 59, 70, 74, 76, 87, 88, 89, 91, 92, 93, 96, 98, 99, 102, 107, 112, 115, 116, 124, 125, 127, 131, 132, 135, 139, 140, 145, 147 or 148 of SEQ ID NO:1, or any combination thereof. In some embodiments, the amino acids substitutions can be at one or more, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 or 34 positions corresponding to residue 33, 37, 45, 49, 50, 59, 70, 74, 76, 87, 88, 89, 91, 92, 93, 96, 98, 99, 102, 107, 112, 115, 116, 124, 125, 127, 131, 132, 135, 139, 140, 145, 147 or 148 of SEQ ID NO:1, or any combination thereof.

In particular embodiments, the PD-1 variant polypeptide of the invention comprises or consists of the amino acid sequence of SEQ ID NO:2 or a fragment thereof (e.g., a fragment with ligand binding affinity) and at least 1 or more amino acid substitutions, e.g., 1, 2, 3, 4, 5, 6, 7, 8, 9, 10, 11, 12, 13, 14, or 15 or more amino acid substitutions. In some instances, the amino acid substitutions are in one or more positions corresponding to residue 33, 37, 45, 49, 50, 59, 70, 74, 76, 87, 88, 89, 91, 92, 93, 96, 98, 99, 102, 107, 112, 115, 116, 124, 125, 127, 131, 132, 135, 139, 140, 145, 147 or 148 of SEQ ID NO:1, or any combination thereof.

In some embodiments, the PD-1 variant polypeptide has at least about 50% or more e.g., about 50%, 55%, 60%, 65%, 70%, 75%, 80%, 85%, 90%, 95%, 96%, 97%, 98%, 99% or more sequence identity to the amino acid sequence of SEQ ID NO:1 or SEQ ID NO:2. In other embodiments, the PD-1 variant polypeptide has at least about 80% or more, e.g., about 80%, 85%, 90%, 95%, 96%, 97%, 98%, 99% or more sequence identity to the amino acid sequence of SEQ ID NO:1 or SEQ ID NO:2. In some instances, the PD-1 variant polypeptide has at least about 80% or more, e.g., about 80%, 81%, 82%, 83%, 84%, 85%, 86%, 87%, 88%, 89%, 90%, 91%, 92%, 93%, 94%, 95%, 96%, 97%, 98%, 99% or more sequence identity to the amino acid sequence of SEQ ID NOS:3-29.

In other embodiments, the PD-1 variant polypeptide has at least about 50% or more, e.g., about 50%, 55%, 60%, 65%, 70%, 75%, 80%, 85%, 90%, 95%, 96%, 97%, 98%, 99% or more of the length of the amino acid sequence of SEQ ID NO:1 or SEQ ID NO:2. In some instances, the PD-1 variant polypeptide has at least about 80% or more, e.g., about 80%, 81%, 82%, 83%, 84%, 85%, 86%, 87%, 88%, 89%, 90%, 91%, 92%, 93%, 94%, 95%, 96%, 97%, 98%, 99% or more of the length of the amino acid sequence of SEQ ID NOS:3-29.

In some embodiments, the PD-1 variant polypeptide has the amino acid sequence of SEQ ID NO:2 and an amino acid substitution at one or more amino acid positions relative to residue 33, 37, 45, 49, 50, 59, 70, 74, 76, 87, 88, 89, 91, 92, 93, 96, 98, 99, 102, 107, 112, 115, 116, 124, 125, 127, 131, 132, 135, 139, 140, 145, 147 or 148 of the amino acid sequence of wild-type PD-1 (SEQ ID NO:1).

In some embodiments, the PD-1 variant polypeptide comprises or consists of the amino acid sequence of SEQ ID NO:2 or a ligand binding fragment thereof and comprises one or more amino acid substitutions at positions N33, F37, T45, N49, A50, T59, M70, N74, S87, Q88, P89, Q91, D92, C93, R96, T98, Q99, N102, H107, R112, R115, N116, G124, A125, S127, K131, A132, K135, R139, A140, T145, R147, R148, or any combination thereof relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises one or more amino acid substitutions including, but not limited to, N33D or N33S, F37L, T45A, N49S, A50V, T59A, M70V or M70I, N74D or N74S, T76A, S87G, Q88R, P89L or P89S, Q91R, D92A or D92G, C93S or C93R, R96G, T98I, Q99A or Q99R, N102S, H107R, R112G, R115G, N116D or N116S, G124S, A125V, S127F or S127L or S127V, K131R, A132I or A132V, K135R, R139G, A140V, T145A or T145I, R147K, and R148G of SEQ ID NO:1 or any combination thereof. In some cases, the PD-1 variant polypeptide comprises one or more amino acid substitutions of SEQ ID NO: 29, wherein the amino acid substitution(s) correspond to N33D or N33S, F37L, T45A, N49S, A50V, T59A, M70V or M70I, N74D or N74S, T76A, S87G, Q88R, P89L or P89S, Q91R, D92A or D92G, C93S or C93R, R96G, T98I, Q99A or Q99R, N102S, H107R, R112G, R115G, N116D or N116S, G124S, A125V, S127F or S127L or S127V, K131R, A132I or A132V, K135R, R139G, A140V, T145A or T145I, R147K, R148G, or any combination thereof of SEQ ID NO:1.

In some embodiments, the PD-1 variant polypeptide has an amino acid modification at a position corresponding to residue 93 of the wild-type PD-1 amino acid sequence set forth in SEQ ID NO:1 (e.g., C93S). In other embodiments, the PD-1 variant polypeptide has an amino acid modification at a position corresponding to residue 132 of the wild-type PD-1 amino acid sequence set forth in SEQ ID NO:1 (e.g., A132I or A132V), and optionally, a C93S substitution. In other embodiments, the PD-1 variant polypeptide has amino acid modifications at positions corresponding to residue 132 of SEQ ID NO:1 (e.g., A132I or A132V), and residue 135 of SEQ ID NO:1 (e.g., K135R), and optionally, a C93S substitution. In yet other embodiments, the PD-1 variant polypeptide has amino acid modifications at positions corresponding to residue 132 of SEQ ID NO:1 (e.g., A132I or A132V), residue 135 of SEQ ID NO:1 (e.g., K135R), and residue 140 of SEQ ID NO:1 (e.g., A140V), and optionally, a C93S substitution. Alternatively, additional amino acid substitutions can include, but are not limited to, N33D or N33S, F37L, T45A, N49S, A50V, T59A, M70V or M70I, N74D or N74S, T76A, S87G, Q88R, P89L or P89S, Q91R, D92A or D92G, R96G, T98I, Q99A or Q99R, N102S, H107R, R112G, R115G, N116D or N116S, G124S, A125V, S127F or S127L or S127V, K131R, R139G, T145A or T145I, R147K, and R148G of SEQ ID NO:1 or any combination thereof.

In some embodiments, the PD-1 variant polypeptide comprises or consists of the amino acid sequence of SEQ ID NO:2 or a ligand binding fragment thereof and comprises an amino acid substitution at position A132 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises an A132V amino acid substitution relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:3.

In some embodiments, the PD-1 variant polypeptide comprises or consists of the amino acid sequence of SEQ ID NO:2 or a ligand binding fragment thereof and comprises amino acid substitutions at positions S87, T98, and A132 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions S87G, T98I, and A132V relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:4.

In some embodiments, the PD-1 variant polypeptide comprises or consists of the amino acid sequence of SEQ ID NO:2 or a ligand binding fragment thereof and comprises amino acid substitutions at positions N116, A132 and T145 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions N116S, A132V and T145I relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:5.

In some embodiments, the PD-1 variant polypeptide comprises or consists of the amino acid sequence of SEQ ID NO:2 or a ligand binding fragment thereof and comprises amino acid substitutions at positions M70, Q88, Q99, R112, N116, and A132 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions M70V, Q88R, Q99R, R112G, N116S, and A132V relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:6.

In some embodiments, the PD-1 variant polypeptide comprises or consists of the amino acid sequence of SEQ ID NO:2 or a ligand binding fragment thereof and comprises amino acid substitutions at positions T59, N74, S87, P89, and A132 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions T59A, N74D, S87G, P89L, and A132I relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:7.

In some embodiments, the PD-1 variant polypeptide comprises or consists of the amino acid sequence of SEQ ID NO:2 or a ligand binding fragment thereof and comprises amino acid substitutions at positions H107, N116, G124, and A132 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions H107R, N116S, G124S, and A132V relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:8.

In some embodiments, the PD-1 variant polypeptide comprises or consists of the amino acid sequence of SEQ ID NO:2 or a ligand binding fragment thereof and comprises amino acid substitutions at positions A132 and A140 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions A132V and A140V relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:9.

In some embodiments, the PD-1 variant polypeptide comprises or consists of the amino acid sequence of SEQ ID NO:2 or a ligand binding fragment thereof and comprises amino acid substitutions at positions N33, N116, and A132 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions N33D, N116D, and A132I relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:10.

In some embodiments, the PD-1 variant polypeptide comprises or consists of the amino acid sequence of SEQ ID NO:2 or a ligand binding fragment thereof and comprises amino acid substitutions at positions R115, N116, A132 and A140 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions R115G, N116D, A132V and A140V relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:11.

In some embodiments, the PD-1 variant polypeptide comprises or consists of the amino acid sequence of SEQ ID NO:2 or a ligand binding fragment thereof and comprises amino acid substitutions at positions N33, S127, K131, A132, K135, R139, R147, and R148 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions N33D, S127L, K131R, A132I, K135R, R139G, R147K, and R148G relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:12.

In some embodiments, the PD-1 variant polypeptide comprises or consists of the amino acid sequence of SEQ ID NO:2 or a ligand binding fragment thereof and comprises amino acid substitutions at positions P89, A132, K135, and A140 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions P89L, A132V, K135R, and A140V relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:13.

In some embodiments, the PD-1 variant polypeptide comprises or consists of the amino acid sequence of SEQ ID NO:2 or a ligand binding fragment thereof and comprises amino acid substitutions at positions N49, T76, R112, N116, G124, A132, K135 and T145 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions N49S, T76A, R112G, N116S, G124S, A132V, K135R and T145A relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:14.

In some embodiments, the PD-1 variant polypeptide comprises or consists of the amino acid sequence of SEQ ID NO:2 or a ligand binding fragment thereof and comprises amino acid substitutions at positions N74, Q88, R112, A132 and K135 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions N74D, Q88R, R112G, A132V and K135R relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:15.

In some embodiments, the PD-1 variant polypeptide comprises or consists of the amino acid sequence of SEQ ID NO:2 or a ligand binding fragment thereof and comprises amino acid substitutions at positions F37, N116, and A132 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions F37L, N116D, and A132V relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:16.

In some embodiments, the PD-1 variant polypeptide comprises or consists of the amino acid sequence of SEQ ID NO:2 or a ligand binding fragment thereof and comprises amino acid substitutions at positions R112 and A132 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions R112G and A132I relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:17.

In some embodiments, the PD-1 variant polypeptide comprises or consists of the amino acid sequence of SEQ ID NO:2 or a ligand binding fragment thereof and comprises amino acid substitutions at positions T45, C93, N102, S127, K131 and A132 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions T45A, C93R, N102S, S127F, K131R and A132I relative to SEQ ID NO:1. In particular embodiments, the PD-1 variant polypeptide comprises or consists of the amino acid sequence of SEQ ID NO:18.

In some embodiments, the PD-1 variant polypeptide comprises or consists of the amino acid sequence of SEQ ID NO:2 or a ligand binding fragment thereof and comprises amino acid substitutions at positions N74 and A132 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions N74S and A132V relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:19.

In some embodiments, the PD-1 variant polypeptide comprises or consists of the amino acid sequence of SEQ ID NO:2 or a ligand binding fragment thereof and comprises amino acid substitutions at positions N33, F37, A50, S87, Q91, and A132 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions N33S, F37L, A50V, S87G, Q91R, and A132V relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:20.

In some embodiments, the PD-1 variant polypeptide comprises or consists of the amino acid sequence of SEQ ID NO:2 or a ligand binding fragment thereof and comprises amino acid substitutions at positions N74, N116, A125, A132, and T145 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions N74S, N116S, A125V, A132V, and T145I relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:21.

In particular embodiments, the PD-1 variant polypeptides of the present invention can comprise or consist of the amino acid sequence of SEQ ID NO:2 or a fragment thereof such as a fragment that binds to one or more PD-1 ligands (e.g., PD-L1 and/or PD-L2) and can have one or any combination of 2, 3, 4, 5, 6, 7, 8, 9, 10, 11, 12, 13, 14, 15, 16, 17, 18, 19, 20, 21, 22, 23, 24, 25, 26, 27, 28, 20, 30, 31, or all 32 of the amino acid modifications shown in Table 1. Table 1 shows unique amino acid substitutions within the sequence of the PD-1 variant polypeptides provided herein. The amino acids listed as SEQ ID NO:1 indicate the amino acid residues at specific positions in the wild-type PD-1 polypeptide (e.g., human wild-type PD-1 polypeptide). In the subsequent rows, amino acid mutations present in the given PD-1 mutant are specified. Absence of an amino acid (e.g., a blank cell in the table) represents that this residue is not mutated from the wild-type residue.

In certain embodiments, the PD-1 variant polypeptides of the present invention are selected from the group of polypeptides set forth in Table 1 (SEQ ID NOS:3-21) and include any combinations thereof.

TABLE 1

Exemplary PD-1 variant polypeptides

| SEQ ID NO. | bp (Ig1) | AA (Ig1) | Amino acid substitutions relative to wild-type PD-1 as set forth in SEQ ID NO:1 | | | | | | | | | | | | | | | | | |
|---|---|---|---|---|---|---|---|---|---|---|---|---|---|---|---|---|---|---|---|---|
| | | | 33 | 37 | 45 | 49 | 50 | 59 | 70 | 74 | 76 | 87 | 88 | 89 | 91 | 93 | 98 | 99 | 102 | 107 |
| 1 | | | N | F | T | N | A | T | M | N | T | S | Q | P | Q | C | T | Q | N | H |
| 2 | | | | | | | | | | | | | | | | | | | | |
| 3 | 1 | 1 | | | | | | | | | | | | | | S | | | | |
| 4 | 3 | 3 | | | | | | | | | G | | | | | S | I | | | |
| 5 | 3 | 3 | | | | | | | | | | | | | | S | | | | |
| 6 | 6 | 6 | | | | | | | V | | | R | | | | S | | R | | |
| 7 | 6 | 5 | | | | | A | | | D | | G | | | L | S | | | | |
| 8 | 5 | 4 | | | | | | | | | | | | | | S | | | | R |
| 9 | 3 | 2 | | | | | | | | | | | | | | S | | | | |
| 10 | 5 | 3 | D | | | | | | | | | | | | | S | | | | |
| 11 | 5 | 4 | | | | | | | | | | | | | | S | | | | |
| 9 | 2 | 2 | | | | | | | | | | | | | | S | | | | |
| 12 | 11 | 8 | D | | | | | | | | | | | | | S | | | | |
| 13 | 4 | 4 | | | | | | | | | | | | | L | S | | | | |
| 14 | 12 | 8 | | | | S | | | | | | A | | | | S | | | | |
| 15 | 6 | 5 | | | | | | | | D | | R | | | | S | | | | |
| 16 | 5 | 3 | | L | | | | | | | | | | | | S | | | | |
| 17 | 3 | 2 | | | | | | | | | | | | | | S | | | | |
| 3 | 2 | 1 | | | | | | | | | | | | | | S | | | | |
| 18 | 8 | 6 | | | A | | | | | | | | | | | R | | S | | |
| 19 | 2 | 2 | | | | | | | | | S | | | | | S | | | | |
| 20 | 8 | 6 | S | L | | | V | | | | | G | | | R | S | | | | |
| 21 | 5 | 5 | | | | | | | | S | | | | | | S | | | | |

TABLE 1-continued

Exemplary PD-1 variant polypeptides

| SEQ ID NO. | bp (Ig1) | AA (Ig1) | 33 | 37 | 45 | 49 | 50 | 59 | 70 | 74 | 76 | 87 | 88 | 89 | 91 | 93 | 98 | 99 | 102 | 107 | 112 | 115 | 116 | 124 | 125 | 127 | 131 | 132 | 135 | 139 | 140 | 145 | 147 | 148 | # of repeats |
|---|---|---|---|---|---|---|---|---|---|---|---|---|---|---|---|---|---|---|---|---|---|---|---|---|---|---|---|---|---|---|---|---|---|---|---|
| 1 | | | | | | | | | | | | | | | | | | | | | G | A | S | K | A | K | R | R | A | T | R | R | | | |
| 2 | | | | | | | | | | | | | | | | | | | | | | | | | | | | | | | | | | | |
| 3 | 1 | 1 | | | | | | | | | | | | | | | | | | | | | | | | | | | V | | | | | | | 2 |
| 4 | 3 | 3 | | | | | | | | | | | | | | | | | | | | | | | | | | | | V | | | | | | | 1 |
| 5 | 3 | 3 | | | | | | | | | | | | | | | | | | | | | | | S | | | | V | | | I | | | | 1 |
| 6 | 6 | 6 | | | | | | | | | | | | | | | | | | | | | G | S | | | | | V | | | | | | | 1 |
| 7 | 6 | 5 | | | | | | | | | | | | | | | | | | | | | | | | | | | I | | | | | | | 6 |
| 8 | 5 | 4 | | | | | | | | | | | | | | | | | | | | | | | S | S | | | V | | | | | | | 2 |
| 9 | 3 | 2 | | | | | | | | | | | | | | | | | | | | | | | | | | | V | | | V | | | | 3 |
| 10 | 5 | 3 | | | | | | | | | | | | | | | | | | | | | | | D | | | | I | | | | | | | 1 |
| 11 | 5 | 4 | | | | | | | | | | | | | | | | | | | | | G | | D | | | | V | | | V | | | | 1 |
| 9 | 2 | 2 | | | | | | | | | | | | | | | | | | | | | | | | | | | V | | | V | | | | 2 |
| 12 | 11 | 8 | | | | | | | | | | | | | | | | | | | | | | | | | L | R | I | R | G | | K | G | | 1 |
| 13 | 4 | 4 | | | | | | | | | | | | | | | | | | | | | | | | | | | V | R | | V | | | | 3 |
| 14 | 12 | 8 | | | | | | | | | | | | | | | | | | | | G | S | S | | | | | V | R | | A | | | | 1 |
| 15 | 6 | 5 | | | | | | | | | | | | | | | | | | | | G | | | | | | | V | R | | | | | | 1 |
| 16 | 5 | 3 | | | | | | | | | | | | | | | | | | | | | | | D | | | | V | | | | | | | 1 |
| 17 | 3 | 2 | | | | | | | | | | | | | | | | | | | | G | | | | | | | I | | | | | | | 1 |
| 3 | 2 | 1 | | | | | | | | | | | | | | | | | | | | | | | | | | | V | | | | | | | 1 |
| 18 | 8 | 6 | | | | | | | | | | | | | | | | | | | | | | | | | F | R | I | | | | | | | 2 |
| 19 | 2 | 2 | | | | | | | | | | | | | | | | | | | | | | | | | | | V | | | | | | | 1 |
| 20 | 8 | 6 | | | | | | | | | | | | | | | | | | | | | | | | | | | V | | | | | | | 1 |
| 21 | 5 | 5 | | | | | | | | | | | | | | | | | | | | | | | S | | V | | V | | | I | | | | 1 |
| | | | | | | | | | | | | | | | | | | | | | | | | | | | | | | | | TOTAL READS: | | | 34 | bp = number of DNA mismatches.
AA = number of amino acid mutations.
Note that some of the DNA mutations are silent.
Total number of times a particular clone appeared is indicated in the right column.

In some embodiments, the PD-1 variant polypeptide comprises or consists of the amino acid sequence of SEQ ID NO:2 or a ligand binding fragment thereof and comprises amino acid substitutions at positions S87, P89, N116, G124, S127, A132, and A140 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions S87G, P89L, N116S, G124S, S127V, A132I, and A140V relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:22.

In some embodiments, the PD-1 variant polypeptide comprises or consists of the amino acid sequence of SEQ ID NO:2 or a ligand binding fragment thereof and comprises amino acid substitutions at positions S87, Q91, H107, N116, G124, S127, A132, R139, R147 and R148 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions S87G, Q91R, H107R, N116S, G124S, S127L, A132I, R139G, R147K and R148G relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:23.

In some embodiments, the PD-1 variant polypeptide comprises or consists of the amino acid sequence of SEQ ID NO:2 or a ligand binding fragment thereof and comprises amino acid substitutions at positions S87, P89, N116, G124, S127, A132, and A140 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions S87G, P89L, N116S, G124S, S127L, A132I, and A140V relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:24.

In some embodiments, the PD-1 variant polypeptide comprises or consists of the amino acid sequence of SEQ ID NO:2 or a ligand binding fragment thereof and comprises amino acid substitutions at positions S87, P89, D92, N116, G124, S127, K131, A132, K135, and A140 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions S87G, P89L, D92A, N116S, G124S, S127L, K131R, A132I, K135R, and A140V relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:25.

In some embodiments, the PD-1 variant polypeptide comprises or consists of the amino acid sequence of SEQ ID NO:2 or a ligand binding fragment thereof and comprises amino acid substitutions at positions S87, P89, D92, R96, Q99, N116, G124, A132, and A140 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions S87G, P89S, D92G, R96G, Q99R, N116S, G124S, A132V, and A140V relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:26.

In some embodiments, the PD-1 variant polypeptide comprises or consists of the amino acid sequence of SEQ ID NO:2 or a ligand binding fragment thereof and comprises amino acid substitutions at positions M70, S87, P89, N116, G124, S127, K131, A132, K135, R139, A140 and R147 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions M70I, S87G, P89L, N116S, G124S, S127L, K131R, A132I, K135R, R139G, A140V and R147K relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:27.

In some embodiments, the PD-1 variant polypeptide comprises or consists of the amino acid sequence of SEQ ID NO:2 or a ligand binding fragment thereof and comprises amino acid substitutions at positions S87, P89, N116, G124, S127, K131, A132, and A140 relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions S87G, P89L, N116S, G124S, S127V, K131R, A132I, and A140V relative to SEQ ID NO:1. In any of these embodiments, the PD-1 variant polypeptide can further comprise a C93 amino acid substitution (e.g., C93S) relative to SEQ ID NO:1. In particular embodiments, the PD-1 variant polypeptide comprises or consists of the amino acid sequence of SEQ ID NO:28.

In certain embodiments, the PD-1 variant polypeptides of the present invention are selected from the group of polypeptides set forth in Table 2 (SEQ ID NOS:22-28) and include any combinations thereof.

TABLE 2

Additional exemplary PD-1 variant polypeptides

| SEQ ID NO. | Clone | bp (Ig1) | AA (Ig1) | \multicolumn{19}{c}{Amino acid substitutions relative to wild-type PD-1 as set forth in SEQ ID NO:1} |
|---|---|---|---|---|---|---|---|---|---|---|---|---|---|---|---|---|---|---|---|---|---|---|
| | | | | 70 | 87 | 89 | 91 | 92 | 93 | 96 | 99 | 107 | 116 | 124 | 127 | 131 | 132 | 135 | 139 | 140 | 147 | 148 |
| 1 | WT PD-1 | | | M | S | P | Q | D | C | R | Q | H | N | G | S | K | A | K | R | A | R | R |
| 22 | 55.1 | 10 | 7 | | G | L | | | S | | | | S | S | V | I | | | | V | | |
| 23 | S5.4 | 13 | 10 | | G | | R | | S | | | R | S | S | L | I | | | G | | K | G |
| 24 | S5.7 | 9 | 7 | | G | L | | | S | | | | S | S | L | I | | | | V | | |
| 25 | S6.8.3 | 12 | 10 | | G | L | | A | S | | | | S | S | L | R | I | R | | V | | |
| 26 | S6.12.4 | 9 | 9 | | G | L | | G | S | G | R | | S | S | | | V | | | V | | |
| 27 | S6.12.6 | 13 | 12 | I | G | L | | | S | | | | S | S | L | R | I | R | G | V | K | |
| 28 | S6.12.9 | 10 | 8 | | G | L | | | S | | | | S | S | V | R | I | | | V | | |

In some embodiments, the PD-1 variant polypeptide comprises or consists of the amino acid sequence of SEQ ID NO:2 or a ligand binding fragment thereof and comprises amino acid substitutions (2 amino acid substitutions) at positions S87 and P89, S87 and N116, S87 and G124, S87 and S127, S87 and A132, S87 and A140, P89 and N116, P89 and G124, P89 and S127, P89 and A132, P89 and A140, N116 and G124, N116 and S127, N116 and A132, N116 and A140, G124 and S127, G124 and A132, G124 and A140, S127 and A132, S127 and A140, A132 and A140, and the like relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions S87G and P89L/S, S87G and N116S, S87G and G124S, S87G and S127L/V, S87G and A132I/V, S87G and A140V, P89L/S and N116S, P89L/S and G124S, P89L/S and S127L/V, P89L/S and A132I/V, P89L/S and A140V, N116S and G124S, N116S and S127L/V, N116S and A132I/V, N116S and A140V, G124S and S127L/V, G124S and A132I/V, G124S and A140V, S127L/V and A132I/V, S127L/V and A140V, A132I/V and A140V, and the like relative to SEQ ID NO:1. In any of these embodiments, the PD-1 variant polypeptide can further comprise a C93 amino acid substitution (e.g., C93S) relative to SEQ ID NO:1.

In some embodiments, the PD-1 variant polypeptide comprises or consists of the amino acid sequence of SEQ ID NO:2 or a ligand binding fragment thereof and comprises amino acid substitutions (3 amino acid substitutions) at positions S87 and P89 and N116; S87 and P89 and G124; S87 and P89 and S127; S87 and P89 and A132; S87 and P89 and A140; S87 and N116 and G124; S87 and N116 and S127; S87 and N116 and A132; S87 and N116 and A140; S87 and G124 and S127; S87 and G124 and A132; S87 and G124 and A140; S87 and S127 and A132; S87 and S127 and A140; S87 and A132 and A140; P89 and N116 and G124; P89 and N116 and S127; P89 and N116 and A132; P89 and N116 and A140; P89 and G124 and S127; P89 and G124 and A132; P89 and G124 and A140; P89 and S127 and A132;

P89 and S127 and A140; P89 and A132 and A140; N116 and G124 and S127; N116 and G124 and A132; N116 and G124 and A140; N116 and S127 and A132; N116 and S127 and A140; N116 and A132 and A140; G124 and S127 and A132; G124 and S127 and A140; G124 and A132 and A140; S127 and A132 and A140; and the like relative to the wild-type PD-1 amino acid sequence set forth in SEQ ID NO:1. In other embodiments, the PD-1 variant polypeptide comprises or consists of the amino acid sequence of SEQ ID NO:2 or a ligand binding fragment thereof and comprises amino acid substitutions S87G and P89L/S and N116S; S87G and P89L/S and G124S; S87G and P89L/S and S127L/V; S87G and P89L/S and A132I/V; S87G and P89L/S and A140V; S87G and N116S and G124S; S87G and N116S and S127L/V; S87G and N116S and A132I/V; S87G and N116S and A140V; S87G and G124S and S127L/V; S87G and G124S and A132I/V; S87G and G124S and A140V; S87G and S127L/V and A132I/V; S87G and S127L/V and A140V; S87G and A132I/V and A140V; P89L/S and N116S and G124S; P89L/S and N116S and S127L/V; P89L/S and N116S and A132I/V; P89L/S and N116S and A140V; P89L/S and G124S and S127L/V; P89L/S and G124S and A132I/V; P89L/S and G124S and A140V; P89L/S and S127L/V and A132I/V; P89L/S and S127L/V and A140V; P89L/S and A132I/V and A140V; N116S and G124S and S127L/V; N116S and G124S and A132I/V; N116S and G124S and A140V; N116S and S127L/V and A132I/V; N116S and S127L/V and A140V; N116S and A132I/V and A140V; G124S and S127L/V and A132I/V; G124S and S127L/V and A140V; G124S and A132I/V and A140V; S127L/V and A132I/V and A140V, and the like relative to SEQ ID NO:1. In any of these embodiments, the PD-1 variant polypeptide can further comprise a C93 amino acid substitution (e.g., C93S) relative to SEQ ID NO:1.

In some embodiments, the PD-1 variant polypeptide comprises or consists of the amino acid sequence of SEQ ID NO:2 or a ligand binding fragment thereof and comprises amino acid substitutions (4 amino acid substitutions) at positions S87 and P89 and N116 and G124; S87 and P89 and N116 and S127; S87 and P89 and N116 and A132; S87 and P89 and N116 and A140; S87 and P89 and G124 and S127; S87 and P89 and G124 and A132; S87 and P89 and G124 and A140; S87 and P89 and S127 and A132; S87 and P89 and S127 and A140; S87 and N116 and G124 and S127; S87 and N116 and G124; and A132; S87 and N116 and G124; and A140; S87 and G124 and S127 and A132; S87 and G124 and S127 and A140; S87 and S127 and A132 and A140; P89 and N116 and G124 and S127; P89 and N116 and G124 and A132; P89 and N116 and G124 and A140; P89 and G124 and S127 and A132; P89 and G124 and S127 and A140; and the like relative to SEQ ID NO:1. In other embodiments, the PD-1 variant polypeptide comprises or consists of the amino acid sequence of SEQ ID NO:2 or a ligand binding fragment thereof and comprises amino acid substitutions S87G and P89L/S and N116S and G124S; S87G and P89L/S and N116S and S127L/V; S87G and P89L/S and N116S and A132I/V; S87G and P89L/S and N116S and A140V; S87G and P89L/S and G124S and S127L/V; S87G and P89L/S and G124S and A132I/V; S87G and P89L/S and G124S and A140V; S87G and P89L/S and S127L/V and A132I/V; S87G and P89L/S and S127L/V and A140V; S87G and N116S and G124S and S127L/V; S87G and N116S and G124S; and A132I/V; S87G and N116S and G124S; and A140V; S87G and G124S and S127L/V and A132I/V; S87G and G124S and S127L/V and A140V; S87G and S127L/V and A132I/V and A140V; P89L/S and N116S and G124S and S127L/V; P89L/S and N116S and G124S and A132I/V; P89L/S and N116S and G124S and N116S and G124S and A140V; P89L/S and G124S and S127L/V and A132I/V; P89L/S and G124S and S127L/V and A140V; and the like relative to SEQ ID NO:1. In any of these embodiments, the PD-1 variant polypeptide can further comprise a C93 amino acid substitution (e.g., C93S) relative to SEQ ID NO:1.

In some embodiments, the PD-1 variant polypeptide comprises or consists of the amino acid sequence of SEQ ID NO:2 or a ligand binding fragment thereof and comprises amino acid substitutions (5 amino acid substitutions) at positions S87 and P89 and N116 and G124 and S127; S87 and P89 and N116 and G124 and A132; S87 and P89 and N116 and G124 and A140; S87 and P89 and N116 and G124 and S127; S87 and P89 and N116 and G124 and A132; S87 and P89 and N116 and G124 and A140; S87 and P89 and G124 and S127 and A132; S87 and P89 and G124 and S127 and A140; S87 and P89 and S127 and A132 and A140; S87 and N116 and G124 and S127 and A132; S87 and N116 and G124 and S127 and A140; S87 and G124 and S127 and A132 and A140; P89 and N116 and G124 and S127 and A132; P89 and N116 and G124 and S127 and A140; N116 and G124 and S127 and A132 and A140; and the like relative to SEQ ID NO:1. In other embodiments, the PD-1 variant polypeptide comprises or consists of the amino acid sequence of SEQ ID NO:2 or a ligand binding fragment thereof and comprises amino acid substitutions S87G and P89L/S and N116S and G124S and S127L/V; S87G and P89L/S and N116S and G124S and A132I/V; S87G and P89L/S and N116S and G124S and A140V; S87G and P89L/S and N116S and G124S and S127L/V; S87G and P89L/S and N116S and G124S and A132I/V; S87G and P89L/S and N116S and G124S and A140V; S87G and P89L/S and G124S and S127L/V and A132I/V; S87G and P89L/S and G124S and S127L/V and A140V; S87G and P89L/S and S127L/V and A132I/V and A140V; S87G and N116S and G124S and S127L/V and A132I/V; S87G and N116S and G124S and S127L/V and A140V; S87G and G124S and S127L/V and A132I/V and A140V; P89L/S and N116S and G124S and S127L/V and A132I/V; P89L/S and N116S and G124S and S127L/V and A140V; N116S and G124S and S127L/V and A132I/V and A140V; and the like relative to SEQ ID NO:1. In any of these embodiments, the PD-1 variant polypeptide can further comprise a C93 amino acid substitution (e.g., C93S) relative to SEQ ID NO:1.

In some embodiments, the PD-1 variant polypeptide comprises or consists of the amino acid sequence of SEQ ID NO:2 or a ligand binding fragment thereof and comprises amino acid substitutions (6 amino acid substitutions) at positions S87 and P89 and N116 and G124 and S127 and A132; S87 and P89 and N116 and G124 and S127 and A140; S87 and P89 and N116 and S127 and A132 and A140; S87 and P89 and G124 and S127 and A132 and A140; S87 and N116 and G124 and S127 and A132 and A140; P89 and N116 and G124 and S127 and A132 and A140; and the like relative to SEQ ID NO:1. In other embodiments, the PD-1 variant polypeptide comprises or consists of the amino acid sequence of SEQ ID NO:2 or a ligand binding fragment thereof and comprises amino acid substitutions S87G and P89L/S and N116S and G124S and S127L/V and A132I/V; S87G and P89L/S and N116S and G124S and S127L/V and A140V; S87G and P89L/S and N116S and S127L/V and A132I/V and A140V; S87G and P89L/S and G124 and S127L/V and A132I/V and A140V; S87G and N116S and G124S and S127L/V and A132I/V and A140V; P89L/S and N116S and G124S and S127L/V and A132I/V and A140V; and the like relative to SEQ ID NO:1. In any of these embodiments, the PD-1 variant polypeptide can further comprise a C93 amino acid substitution (e.g., C93S) relative to SEQ ID NO:1.

In some embodiments, the PD-1 variant polypeptide comprises or consists of the amino acid sequence of SEQ ID NO:2 or a ligand binding fragment thereof and comprises amino acid substitutions (7 amino acid substitutions) at positions S87 and P89 and N116 and G124 and S127 and A132 and A140 relative to SEQ ID NO:1. In other embodiments, the PD-1 variant polypeptide comprises or consists of the amino acid sequence of SEQ ID NO:2 or a ligand binding fragment thereof and comprises amino acid substitutions S87G and P89L/S and N116S and G124S and S127L/V and A132I/V and A140V relative to SEQ ID NO:1. In any of these embodiments, the PD-1 variant polypeptide can further comprise a C93 amino acid substitution (e.g., C93S) relative to SEQ ID NO:1.

Polypeptides useful in the invention, as described herein, include those that are mutated to contain one or more amino acid substitutions, deletions, or insertions. Methods for mutagenesis are known in the art. The mutated or variant polypeptides inhibit or reduce inhibitory signal transduction through PD-1 receptors by binding to ligands of PD-1. The variant polypeptides may be of any species of origin. In some embodiments, the variant polypeptide is from a mammalian species (e.g., canine, bovine, sheep, equine, porcine, rodent, mouse, rat, feline, primate, monkey, ape, chimpanzee, and the like). In other embodiments, the variant polypeptide is of murine or primate origin. In particular embodiments, the variant polypeptide is of human origin.

The amino acids substitutions can include any naturally occurring or man-made amino acid substitution. In some instances, the amino acid substitution is any naturally occurring substitution. The substitution can include replacing an existing amino acid with another amino acid, e.g., a conservative equivalent thereof. In other instances, the amino acid substitution is a non-naturally occurring substitution. For instance, a natural amino acid of the variant polypeptide can be replaced with a non-natural amino acid.

In some embodiments, one or more amino acid modifications can be used to alter properties of the form of PD-1, e.g., affecting the stability, binding activity and/or specificity, etc. Techniques for in vitro mutagenesis of cloned genes are known. Examples of protocols for scanning mutations may be found in Gustin et al., *Biotechniques* 14:22 (1993); Barany, *Gene* 37:111-23 (1985); Colicelli et al., *Mol Gen Genet* 199:537-9 (1985); and Prentki et al., *Gene* 29:303-13 (1984). Methods for site specific mutagenesis can be found in Sambrook et al., Molecular Cloning: A Laboratory Manual, CSH Press 1989, pp. 15.3-15.108; Weiner et al., *Gene* 126:35-41 (1993); Sayers et al., *Biotechniques* 13:592-6 (1992); Jones and Winistorfer, *Biotechniques* 12:528-30 (1992); Barton et al., *Nucleic Acids Res* 18:7349-55 (1990); Marotti and Tomich, *Gene Anal Tech* 6:67-70 (1989); and Zhu, *Anal Biochem* 177:120-4 (1989).

A variant polypeptide can include any combination of amino acid substitutions, deletions or insertions to the PD-1 polypeptide of SEQ ID NO:2 that increases or enhances its binding activity to PD-L1, PD-L2, or both compared to wild-type PD-1. In some cases, the variant polypeptides described herein are extracellular domain fragments of the wild-type PD-1 polypeptide and have any combination of amino acid substitutions, deletions or insertions to wild-type PD-1 polypeptide of SEQ ID NO:1 that maintains or increases/enhances its binding activity to PD-L1, PD-L2, or both compared to wild-type PD-1.

In some cases, a useful PD-1 variant polypeptide specifically binds to PD-L1 and/or PD-L2 on a target cell, e.g., on a cancer cell and thereby reduces (e.g., blocks, prevents, etc.) the interaction between the PD-L1/PD-L2 and PD-1 (e.g., wild-type PD-1 on an immune cell, e.g., on a T cell). Thus, a PD-1 variant polypeptide provided herein can act as an engineered decoy receptor for PD-L1 and/or PD-L2. By reducing the interaction between PD-L1 and/or PD-L2 and wild-type PD-1, the PD-1 variant polypeptide can decrease the immune inhibitory signals produced by the PD-L/PD-1 interaction, and therefore can increase the immune response (e.g., by increasing T cell activation). A suitable PD-1 variant polypeptide can comprises the portion of PD-1 that is sufficient to bind PD-L1 at a recognizable affinity, e.g., high affinity, which normally lies between the signal sequence and the transmembrane domain, or a fragment thereof that retains the binding activity.

In some embodiments, the variant polypeptides of the invention comprise or consist of at least about 5, 10, 15, 20, 25, 30, 40, 50, 60, 70, 75, 80, 90, 100, 110, 120, 130, 140, 150, 160 or more contiguous amino acids of the extracellular domain (residues 1-170) of the wild-type PD-1 polypeptide sequence set forth in SEQ ID NO:1 and one or more amino acid substitutions including, but not limited to, N33D or N33S; F37L; T45A; N49S; A50V; T59A; M70V; N74D or N74S; T76A; S87G; Q88R; P89L; Q91R; C93S or C93R; T98I; Q99R; N102S; H107R; R112G or R115G; N116D or N116S; G124S; A125V; S127L or S127F; K131R; A132I or A132V; K135R; R139G; A140V; T145A or T145I; R147K; or R148G of SEQ ID NO:1, or any combination thereof. In particular embodiments, these variant polypeptides have the desired antagonist activity described herein (e.g., increased or enhanced ligand binding affinity).

In other embodiments, the variant polypeptides of the invention comprise or consist of at least about 5, 10, 15, 20, 25, 30, 40, 50, 60, 70, 75, 80, 90, 100 or more contiguous amino acids of the truncated extracellular domain PD-1 polypeptide sequence set forth in SEQ ID NO:2 and one or more amino acid substitutions at positions corresponding to the wild-type PD-1 polypeptide sequence set forth in SEQ ID NO:1 including, but not limited to, N33D or N33S; F37L; T45A; N49S; A50V; T59A; M70V; N74D or N74S; T76A; S87G; Q88R; P89L; Q91R; C93S or C93R; T98I; Q99R; N102S; H107R; R112G or R115G; N116D or N116S; G124S; A125V; S127L or S127F; K131R; A132I or A132V; K135R; R139G; A140V; T145A or T145I; R147K; or R148G, or any combination thereof. In particular embodiments, these variant polypeptides have the desired antagonist activity described herein (e.g., increased or enhanced ligand binding affinity). An increase in ligand binding affinity can be represented as a decrease of the off-rate by, for example, at least 10-fold, at least 20-fold, at least 50-fold, at least 100-fold, at least 500-fold, or more.

The PD-1 variant polypeptides can be further modified, e.g., joined to a wide variety of other oligopeptides or proteins, for a variety of purposes. For instance, various post-translation or post-expression modifications can be carried out with respect to the PD-1 variants of the present invention. For example, by employing the appropriate coding sequences, one may provide farnesylation or prenylation. In some embodiments, the PD-1 variants can be PEGylated, where the polyethyleneoxy group provides for enhanced lifetime in the blood stream. The PD-1 variants of the present invention can also be combined with other proteins, such as the Fc of an IgG isotype, which can be complement binding, with a toxin, such as ricin, abrin, diphtheria toxin, or the like, or with specific binding agents that allow targeting to specific moieties on a target cell.

In some embodiments, the PD-1 variant polypeptide is a fusion protein, e.g., fused in frame with a second polypeptide. The fusion protein can form a chimeric protein. In some embodiments, the second polypeptide is capable of increasing the size of the fusion protein, e.g., so that the fusion protein will not be cleared from the circulation rapidly. In some other embodiments, the second polypeptide is part or whole of Fc region. In some other embodiments, the second polypeptide is any suitable polypeptide that is substantially similar to Fc, e.g., providing increased size and/or additional binding or interaction with Ig molecules. The fusion proteins can facilitate purification, multimerization, and show an increased half-life in vivo. Fusion proteins having disulfide-linked multimeric structures can also be more efficient in binding and neutralizing other molecules than a monomeric PD-1 variant polypeptide. In yet some other embodiments, the second polypeptide is part or whole of an albumin protein, e.g., a human serum albumin protein. In other embodiments, the second polypeptide is a peptide that facilitates purification of the fused polypeptide, such as but not limited to a hexa-histidine peptide tag or an epitope derived from the influenza hemagglutinin protein.

PD-1 variants described herein can be fused to a heterologous polypeptide. In some embodiments, the variant is fused to an immunoglobulin sequence. The immunoglobulin sequence can be an immunoglobulin constant domain(s). The immunoglobulin moiety in such chimeras may be obtained from any species, usually human, and includes IgG1, IgG2, IgG3 or IgG4 subtypes, IgA, IgE, IgD or IgM. The immunoglobulin moiety may comprise one or more domains, e.g., CH1, CH2, CH3, etc.

The PD-1 variant polypeptide can be monomeric or multimeric, i.e., dimer, trimer, tetramer, etc. For example, the fusion partner provides a multimerization domain such as via any protein-protein domain (e.g., a leucine zipper motif, a synzip polypeptide, a CH3 domain, and the like). In some embodiments, the PD-1 variants include at least two same or different PD-1 variants linked covalently or non-covalently. For example, in some embodiments, the PD-1 variants of the present invention include two, three, four, five, or six same or different PD-1 variants linked covalently, e.g., so that they will have the appropriate size, but avoiding unwanted aggregation.

In some embodiments, the PD-1 variant polypeptide is multispecific (e.g., bispecific). For example, a PD-1 variant polypeptide can be multispecific (e.g., bispecific) such that a first region of the polypeptide corresponds to a PD-1 variant polypeptide sequence (which specifically binds PD-L1 and/or PD-L2), and a second region (the fusion partner) (e.g., an antibody derived sequence, e.g., a binding region of an antibody comprising that CDRs of the antibody; a specific binding polypeptide; a binding portion of a ligand; a binding portion of a receptor, etc.) that specifically binds to another target (e.g., antigen, a receptor, a ligand, etc.). In some cases, a PD-1 variant polypeptide is fused to a second polypeptide (a fusion partner) that binds specifically to a target other than PD-L1 Examples of suitable fusion partners include, but are not limited to cytokines, 41BB-agonists; CD40-agonists; inhibitors of BTLA and/or CD160; inhibitors of TIM3 and/or CEACAM1; and binding sequences from antibodies against cancer cell markers such as CD19, CD20, CD22, CD24, CD25, CD30, CD33, CD38, CD44, CD52, CD56, CD70, CD96, CD97, CD99, CD123, CD279 (PD-1), EGFR, HER2, CD117, C-Met, PTHR2, HAVCR2 (TIM3), etc. Examples of antibodies with CDRs that provide specific binding to a cancer cell marker include, but are not limited to, cetuximab, panitumumab, rituximab, trastuzumab, pertuzumab, alemtuzumab, brentuximab, and the like.

The PD-1 variant polypeptides can be modified to improve their characteristics, such as increasing thermal stability or increasing polypeptide stability during purification from a host cell or subsequent handling and storage. In some embodiments, the melting temperature of the PD-1 variants of the present invention is at least 5° C., 10° C., 15° C., or 20° C. higher than the melting temperature of a wild-type PD-1 polypeptide. In some instances, peptide moieties may be added to the PD-1 variants of the present invention to facilitate purification and subsequently removed prior to final preparation of the polypeptide. The addition of peptide moieties to facilitate handling of polypeptides are familiar and routine techniques in the art.

In some embodiments, the PD-1 variant polypeptides also include one or more modifications that do not alter their primary sequences. For example, such modifications can include chemical derivatization of polypeptides, e.g., acetylation, amidation, carboxylation, prenylation, PEGylation etc. Such modifications can also include modifications of glycosylation, e.g., those made by modifying the glycosylation patterns of a polypeptide during its synthesis and processing or in further processing steps, e.g., by exposing the polypeptide to enzymes which affect glycosylation, such as mammalian glycosylating or deglycosylating enzymes. In some embodiments, the PD-1 variants of the present invention include PD-1 variants having phosphorylated amino acid residues, e.g., phosphotyrosine, phosphoserine, or phosphothreonine.

In some embodiments, the PD-1 variants include variants that are further modified to improve their resistance to proteolytic degradation or to optimize solubility properties or to render them more suitable as a therapeutic agent. For example, PD-1 variants of the present invention further include analogs of a PD-1 variant containing residues other than naturally occurring L-amino acids, e.g., D-amino acids or non-naturally occurring synthetic amino acids. D-amino acids may be substituted for some or all of the amino acid residues.

In some embodiments, the PD-1 variant is coupled or conjugated to one or more detectable labels that can be used for, e.g., imaging or diagnostics. Non-limiting examples of a detectable label include radiography moieties, e.g., heavy metals and radiation emitting moieties, positron emitting moieties, magnetic resonance contrast moieties, and optically visible moieties e.g., fluorescent or visible-spectrum dyes, visible particles, etc.

In some embodiments, the PD-1 variant is coupled or conjugated to one or more therapeutic moieties or cytotoxic moieties such as, but not limited to, a moiety that inhibits cell growth or promotes cell death when proximate to or absorbed by the cell. Suitable cytotoxic moieties include radioactive isotopes (radionuclides), chemotoxic agents such as differentiation inducers and small chemotoxic drugs, toxin proteins, and derivatives thereof.

In particular embodiments, the PD-1 variant polypeptides described herein have a binding affinity to a PD-1 ligand (i.e., PD-L1 and/or PD-L2) that is at least equal or better than the wild-type PD-1 polypeptide. In some embodiments, the PD-1 variants have a binding affinity to PD-L1 and/or PD-L2 that is at least 1-fold, 2-fold, 3-fold, 4-fold, 5-fold, or 6-fold greater than that of the wild-type PD-1 polypeptide. The PD-1 variants can have a binding affinity to PD-L1 that is at least 1-fold, 2-fold, 3-fold, 4-fold, 5-fold, or 6-fold greater than that of the wild-type PD-1 polypeptide. The PD-1 variants can have a binding affinity to PD-L2 that is at least 1-fold, 2-fold, 3-fold, 4-fold, 5-fold, or 6-fold greater than that of the wild-type PD-1 polypeptide.

In certain embodiments, the binding affinity of the PD-1 variant to PD-L1, PD-L2 or both is at least about 0.5%, 1%, 2%, 3%, 4%, 5%, 6%, 7%, 8%, 9%, 10%, 15%, 20%, 25%, 30%, 35%, 40%, 45%, 50% or higher than that of the wild-type PD-1 polypeptide. In other embodiments, the PD-1 variants of the present invention have a binding affinity of less than about $1\times10^{-8}$ M, $1\times10^{-10}$ M or $1\times10^{-10}$ M for PD-L1 and/or PD-L2. The PD-1 variants of the present invention can have a binding affinity of less than about $1\times10^{-8}$ M, $1\times10^{-9}$ M or $1\times10^{-10}$ M for PD-L1. The PD-1 variants of the present invention can have a binding affinity of less than about $1\times10^{-8}$ M, $1\times10^{-9}$ M or $1\times10^{-10}$ M for PD-L2. In yet other embodiments, the PD-1 variants inhibit or compete with wild-type PD-1 binding to PD-L1 and/or PD-L2 either in vivo, in vitro or both.

In some embodiments, the PD-1 variant polypeptide has a dissociation half-life for PD-L1 that is 2-fold or more (e.g., 5-fold or more, 10-fold or more, 100-fold or more, 500-fold or more, 1000-fold or more, 5000-fold or more, $10^4$-fold or more, $10^5$-fold or more, $10^6$-fold or more, $10^7$-fold or more, $10^8$-fold or more, etc.) greater than the dissociation half-life for PD-L1 of a wild type PD-1 protein; and/or 2-fold or more (e.g., 5-fold or more, 10-fold or more, 100-fold or more, 500-fold or more, 1000-fold or more, 5000-fold or more, $10^4$-fold or more, $10^5$-fold or more, $10^6$-fold or more, $10^7$-fold or more, $10^8$-fold or more, etc.) greater than the dissociation half-life for PD-L1 of a PD-1 variant polypeptide that does not have an amino acid substitution relative to a corresponding sequence of a wild type PD-1 polypeptide.

The ability of a molecule to bind to PD-L1 and/or PD-L2 can be determined, for example, by the ability of the putative ligand to bind to PD-L1 and/or PD-L2 coated on an assay plate. In one embodiment, the binding activity of PD-1 variants to PD-L1 and/or PD-L2 can be assayed by either immobilizing the ligand, e.g., PD-L1 and/or PD-L2 or the PD-1 variant. For example, the assay can include immobilizing PD-L1 and/or PD-L2 fused to a His-tag onto Ni-activated NTA resin beads. Agents can be added in an appropriate buffer and the beads incubated for a period of time at a given temperature. After washes to remove unbound material, the bound protein can be released with, for example, SDS, buffers with a high pH, and the like and analyzed.

Alternatively, binding affinity of a PD-1 variant for PD-L1 and/or PD-L2 can be determined by displaying the PD-1 variant on a microbial cell surface, e.g., a yeast cell surface and detecting the bound complex by, for example, flow cytometry. The binding affinity of PD-1 for PD-1 ligands can be measured using any known method recognized in the art including, but not limited to, the method described in Examples 1 and 2, radioactive ligand binding assays, non-radioactive (fluorescent) ligand binding assays, surface plasmon resonance (SPR), such as Biacore™, plasmon-waveguide resonance (PWR), thermodynamic binding assays, whole cell ligand-binding assays, and structure-based ligand binding assays.

Also within the scope of the invention are kits comprising the compositions (e.g., PD-1 variants and formulations thereof) described herein and instructions for use. The kit can further contain a least one additional reagent. Kits typically include a label with instructions indicating the intended use of the contents of the kit. The term label includes any writing or recorded material supplied on or with the kit, or which otherwise accompanies the kit.

B. Methods of Generating PD-1 Variant Polypeptides

The PD-1 variants of the present invention can be produced by any suitable means known or later discovered in the field, e.g., produced from eukaryotic or prokaryotic cells, synthesized in vitro, etc. Where the protein is produced by prokaryotic cells, it may be further processed by unfolding, e.g., heat denaturation, DTT reduction, etc. and may be further refolded, using methods known in the art.

The polypeptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention. Direct chemical synthesis methods include, for example, the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. While chemical synthesis of DNA is often limited to sequences of about 100 bases, longer sequences can be obtained by the ligation of shorter sequences. Alternatively, subsequences may be cloned and the appropriate subsequences cleaved using appropriate restriction enzymes.

The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like. Also provided herein are expression vectors for in vitro or in vivo expression of one or more PD-1 variants of the present invention, either constitutively or under one or more regulatory elements. Also provided is a cell or a cell population comprising one or more expression vectors for expressing PD-1 variants, either constitutively or under one or more regulatory elements.

Methods for producing recombinant polypeptides, nucleic acids encoding recombinant polypeptides, expression vectors and recombinant cells that express recombinant polypeptides are known to those in the art and are described in detail, for example, in Sambrook et al., *Molecular Cloning: A Laboratory Manual*. New York: Cold Spring Harbor Press, 1989.

C. Methods of Treatment

1. Subjects Amenable to Treatment

The increased T cell response achieved as a result of the use of the PD-1 variants of the invention is sufficient to treat a disease or disorder, including but not limited to cancer, viral infection, bacterial infection, fungal infection and parasitic infection. Cancers that can be treated using the PD-1 variants of the invention include, but are not limited to, bladder, brain, breast, bone, cervical, colon, colorectal, esophageal, kidney, liver, lung, nasopharangeal, pancreatic, prostate, rectal, skin, stomach, uterine, ovarian, testicular, or hematologic cancer. The hematologic cancers include multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, precursor T-lymphoblastic lymphoma, and any combination thereof. Non-limiting examples of solid tumors that can be treated with the PD-1 variants of the invention are non-small cell lung cancer, renal cell carcinoma and triple negative breast cancer. Examples of other cancers include cancers of the head and neck, cutaneous or intraocular malignant melanoma, cancer of the fallopian tubes, carcinoma of the endometrium, carcinoma of the cervix, carcinoma of the vagina, carcinoma of the vulva, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers, soft tissue tumors, carcinomas, and any combination thereof. Any cancer is a suitable cancer to be treated by the methods and compositions described herein. In some cases, cells of the cancer express PD-L1. In other cases, cells of the cancer do not express PD-L1, yet can be treated with a PD-1 variant polypeptide.

The methods of the present invention include administering to a subject in need of treatment a therapeutically effective amount of one or more PD-1 variant polypeptides described herein. In some embodiments, the subject has cancer and administration of a therapeutically effective amount of one or more PD-1 variant polypeptides can treat, reduce or prevent metastasis or invasion of a tumor in the subject. In other embodiments, the PD-1 variant polypeptide(s) can reduce or inhibit the growth of a solid tumor in a subject with cancer.

In some embodiments, a subject having an infection, e.g., a local or systemic infection, is administered of a therapeutically effective amount of one or more PD-1 variant polypeptides described herein to treat the infection. In other embodiments, the subject has chronic infectious disease caused by a bacterium, virus, protozoan, parasite, or other microbial pathogen. Non-limiting examples of viral infections that can be treated with one or more PD-1 variant polypeptides include immunodeficiency (e.g., HIV), papilloma (e.g., HPV), herpes (e.g., HSV), encephalitis, influenza (e.g., human influenza virus A), hepatitis (e.g. HCV, HBV), and common cold (e.g., human rhinovirus) viral infections. Non-limiting examples of non-viral infections caused by, but are not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus, Treponema, Vibrio, Yersinia, Cryptococcus neoformans, Histoplasma* sp. (such as *Histoplasma capsulatum*), *Candida albicans, Candida tropicalis, Nocardia asteroides, Rickettsia ricketsii, Rickettsia typhi, Leishmania, Mycoplasma pneumoniae, Chlamydial psittaci, Chlamydial trachomatis, Plasmodium* sp. (such as *Plasmodium falciparum*), *Trypanosoma brucei, Entamoeba histolytica, Toxoplasma gondii, Trichomonas vaginalis* and *Schistosoma mansoni*, can be treated with one or more soluble PD-1 variant polypeptides of the invention.

2. Therapeutic Administration

In certain embodiments, a therapeutically effective composition or formulation comprising one or more PD-1 variant polypeptides of the invention may be administered systemically to the individual in need thereof or via any other route of administration known in the art. Systemic administration includes, but is not limited to, oral, rectal, nasal, vaginal, topical, pulmonary, intranasal, buccal, transdermal, and parenteral (i.e., intramuscular, intravenous and subcutaneous). In accordance with good clinical practice, it is preferred to administer the composition at a dose that will produce desired therapeutic effects without causing undue harmful side effects. It will be appreciated that the extent of tolerable side effects is dependent on the seriousness of the condition being treated. In general, therapeutic levels of 10%, 25%, 50%, 75%, or up to 100% of the maximum tolerated dosage as determined through standard toxicity testing are appropriate.

In some embodiments, a therapeutically effective composition or formulation comprising a nucleic acid encoding one or more PD-1 variant polypeptides of the invention may be introduced in a cell in vivo, ex vivo or in vitro. For instance, a nucleic acid encoding a PD-1 variant polypeptide is introduced into a cell that is in vivo (e.g., introduced into a cell by administering the nucleic acid to an individual). In other instances, a nucleic acid encoding a PD-1 variant polypeptide is introduced into a cell outside an individual (e.g., ex vivo or in vitro), and then the cell is administered to the individual. The cell can be autologous or allogeneic to the individual. The cell can be an immune cell (e.g., a leukocyte, a T cell, a CD8 T cell, a CD4 T cell, a memory/effector T cell, a B cell, an antigen presenting cell (APC), a dendritic cell, a macrophage, a monocyte, an NK cell, and the like). The cell can be a stem cell (e.g., a hematopoietic stem cell, a pluripotent stem cell, a multipotent stem cell, a tissue restricted stem cell, etc.)

In some embodiments, the cell is an immune cell, e.g., a T cell with an engineered T cell receptor (TCR) such as a T cell receptor that is heterologous to the immune cell, e.g., the T cell. In other embodiments, the cell is an immune cell, e.g., a T cell with an engineered chimeric antigen receptor (CAR) such that the immune cell, e.g., the T cell includes a heterologous chimeric antigen receptor that bind to a cancer cell via, for example, a cancer antigen or tumor antigen.

3. Dosing

In some embodiments, an effective dose of the therapeutic entity of the present invention, e.g. for the treatment of metastatic cancer or infection, varies depending upon many different factors, including means of administration, target site, physiological state of the patient, whether the patient is human or an animal, other medications administered, and whether treatment is prophylactic or therapeutic. Treatment dosages can be titrated to optimize safety and efficacy.

In some embodiments, the dosage may range from about 0.0001 to 100 mg/kg, and more usually 0.01 to 5 mg/kg, of the host body weight. For example, dosages can be 1 mg/kg body weight or 10 mg/kg body weight or within the range of 1-10 mg/kg.

An exemplary treatment regime entails administration once a day, once per every two days, once per every week, once per every two weeks, a month, or once every 3 to 6 months. Therapeutic entities of the present invention are usually administered on multiple occasions. Intervals between single dosages can be daily, weekly, monthly or yearly. Intervals can also be irregular as indicated by measuring blood levels of the therapeutic entity in the patient. A daily dose can be administered once per day or divided into subdoses and administered in multiple doses, e.g., twice, three times, or four times per day. However, as will be appreciated by a skilled artisan, the compositions described herein may be administered in different amounts and at different times. The skilled artisan will also appreciate that certain factors may influence the dosage and timing required to effectively treat a subject, including but not limited to the severity of the disease or malignant condition, previous treatments, the general health and/or age of the subject, and other diseases present. Moreover, treatment of a subject with a therapeutically effective amount of a composition can include a single treatment or, preferably, can include a series of treatments.

Alternatively, therapeutic entities can be administered as a sustained release formulation, in which case less frequent administration is required. Dosage and frequency vary depending on the half-life of the polypeptide in the patient.

For prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

For therapeutic applications, therapeutic entities of the present invention are administered to a patient suspected of, or already suffering from such a disease in an amount sufficient to cure, or at least partially arrest, one or more symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient response has been achieved. Typically, the response is monitored and repeated dosages are given if there is a recurrence of the cancer or the infection.

Determination of an effective amount is well within the capability of those skilled in the art, especially in light of the detailed disclosure provided herein. Generally, an efficacious or effective amount of a combination of one or more polypeptides of the present invention is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics*, 11th Edition, 2006, supra; in a *Physicians' Desk Reference* (PDR), 64th Edition, 2010; in *Remington: The Science and Practice of Pharmacy*, 21st Ed., 2006, supra; and in Martindale: *The Complete Drug Reference, Sweetman*, 2005, London: Pharmaceutical Press., and in Martindale, *Martindale: The Extra Pharmacopoeia*, 31st Edition., 1996, Amer Pharmaceutical Assn, each of which are hereby incorporated herein by reference.

Exemplary doses of the pharmaceutical compositions described herein include milligram or microgram amounts of the PD-1 variant per kilogram of subject or sample weight (e.g., about 1 µg/kg to about 500 mg/kg, about 100 µg/kg to about 5 mg/kg, or about 1 µg/kg to about 50 µg/kg. It is furthermore understood that appropriate doses of the PD-1 variant depend upon the potency of the composition with respect to the desired effect to be achieved. When the PD-1 variant(s) are to be administered to a mammal, a physician, veterinarian, or researcher may, for example, prescribe a relatively low dose at first, subsequently increasing the dose until an appropriate response is obtained. In addition, it is understood that the specific dose level for any particular mammal subject will depend upon a variety of factors including the activity of the specific composition employed, the age, body weight, general health, gender, and diet of the subject, the time of administration, the route of administration, the rate of excretion, any drug combination, and the degree of expression or activity to be modulated.

The appropriate dosage of the variant polypeptides of the present invention will vary according to several factors, including the chosen route of administration, the formulation of the composition, patient response, the severity of the condition, the subject's weight, and the judgment of the prescribing physician. The dosage can be increased or decreased over time, as required by an individual patient. Usually, a patient initially is given a low dose, which is then increased to an efficacious dosage tolerable to the patient.

The dosage of PD-1 variant polypeptides administered is dependent on the individual, the body weight, age, individual condition, surface area of the area to be treated and on the form of administration. The size of the dose also will be determined by the existence, nature, and extent of any adverse effects that accompany the administration of a particular compound in a particular subject. A unit dosage for administration to a mammal of about 50 to 70 kg may contain between about 5 and 500 mg of the active ingredient. Typically, a dosage of the PD-1 variant polypeptides, is a dosage that is sufficient to achieve the desired effect.

Optimum dosages, toxicity, and therapeutic efficacy of compositions can further vary depending on the relative potency of individual compositions and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compositions that exhibit large therapeutic indices are preferred. While compositions that exhibit toxic side effects can be used, care should be taken to design a delivery system that targets such compositions to the site of affected tissue to minimize potential damage to normal cells and, thereby, reduce side effects.

The data obtained from, for example, animal studies (e.g., rodents and monkeys) can be used to formulate a dosage range for use in humans. The dosage of polypeptides of the present invention lies preferably within a range of circulating concentrations that include the $ED_{50}$ with little or no toxicity. The dosage can vary within this range depending upon the dosage form employed and the route of administration. For any composition for use in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a polypeptide or composition, is from about 1 ng/kg to 100 mg/kg for a typical subject.

A polypeptide composition of the present invention for intravenous administration can be about 0.1 to 10 mg/kg per patient per day. Dosages from 0.1 up to about 100 mg/kg per patient per day may be used. Actual methods for preparing administrable compositions will be known or apparent to those skilled in the art and are described in more detail in such publications as *Remington: The Science and Practice of Pharmacy*, 21st Ed., 2006, Lippincott Williams & Wilkins.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

D. Pharmaceutical Compositions

Provided herein are pharmaceutical compositions containing one or more of the PD-1 variant polypeptides described herein. These pharmaceutical compositions are suitable for therapeutic use, e.g., for human treatment. In some embodiments, pharmaceutical compositions of the present invention include one or more therapeutic entities of the present invention, e.g., PD-1 variants or pharmaceutically acceptable salts, esters or solvates thereof or any prodrug thereof. In some other embodiments, the pharmaceutical compositions include one or more therapeutic entities of the present invention in combination with a cytotoxic agent, e.g., an anti-tumor agent, an anti-viral agent, an anti-bacterial agent, an anti-fungal agent or an anti-parasitic agent. In yet some other embodiments, the pharmaceutical compositions include one or more of the therapeutic entities in combination with another pharmaceutically acceptable excipient.

The therapeutic entities are often administered as pharmaceutical compositions comprising an active therapeutic agent, i.e., and a variety of other pharmaceutically acceptable components. (See, e.g., *Remington: The Science and Practice of Pharmacy*, 21st Ed., 2006, Lippincott Williams & Wilkins). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, non-immunogenic stabilizers and the like.

In some embodiments, the pharmaceutical compositions described herein can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

Compositions for the treatment of cancer, e.g., metastatic cancer, can be administered by parenteral, topical, intravenous, intratumoral, oral, subcutaneous, intraarterial, intracranial, intraperitoneal, intranasal or intramuscular means. The most typical route of administration is intravenous or intratumoral although other routes can be equally effective.

Compositions can be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect.

The therapeutic formulations may be administered to the subject after a diagnosis of disease. Several divided dosages, as well as staggered dosages, may be administered daily or sequentially, or the dose may be continuously infused, or may be a bolus injection. Further, the dosages of the therapeutic formulations may be proportionally increased or decreased as indicated by the exigencies of the therapeutic situation.

For parenteral administration, compositions of the invention can be administered as injectable dosages of a solution or suspension of the substance in a physiologically acceptable diluent with a pharmaceutical carrier that can be a sterile liquid such as water, oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins. Glenn et al., Nature 391: 851, 1998. Co-administration can be achieved by using the components as a mixture or as linked molecules obtained by chemical crosslinking or expression as a fusion protein.

Alternatively, transdermal delivery can be achieved using a skin patch or using transferosomes. Paul et al., *Eur. J. Immunol.* 25: 3521-24, 1995; Cevc et al., *Biochem. Biophys. Acta* 1368: 201-15, 1998.

The pharmaceutical compositions are generally formulated as sterile, substantially isotonic and in full compliance with all Good Manufacturing Practice (GMP) regulations of the U.S. Food and Drug Administration.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. See, e.g., Fingl et al., 1975, In: The Pharmacological Basis of Therapeutics, Ch. 1.

The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

E. Combination Therapies

In certain embodiments, the PD-1 variant polypeptides of the invention can be administered in combination with one or more additional agents that can enhance or promote an immune response in a subject. Such agents include, but are not limited to, amsacrine, bleomycin, busulfan, capecitabine, carboplatin, carmustine, chlorambucil, cisplatin, cladribine, clofarabine, crisantaspase, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

In some embodiments, the PD-1 variant polypeptide is administered to a subject in need thereof with an agent that can increase the subject's T cell response. In some instances, an agent that reduces the activity of regulatory T lymphocytes (T-regs), e.g., sunitinib (Sutent®), imatinib (Gleevac®), or an anti-TGFβ, can be given.

The treatments provided herein can also be used in conjunction with other types of therapies, such as anticancer drug therapy, chemotherapy, radiation therapy, surgery, other immunotherapy, or other standard-of-care treatments as described in the National Comprehensive Cancer Network Clinical Practice Guidelines in Oncology (NCCN Guidelines®).

Examples of chemotherapeutic agents that can be co-administered with the PD-1 variant include, without limitation, alkylating agents (cisplatin, carboplatin, and oxaliplatin); anti-metabolites (purine or pyrimidine mimetics including for example azathioprine and mercaptopurine); plant alkaloids and terpenoids (vinca alkaloids and taxanes); vinca alkaloids (vincristine, vinblastine, vinorelbine, and vindesine); podophyllotoxin (including etoposide and teniposide); taxanes (paclitaxel, taxol and docetaxel); topoisomerase inhibitors (Type I inhibitors: camptothecins, irinotecan and topotecan; Type II Inhibitors: amsacrine, etoposide, etoposide phosphate, and teniposide); antineoplastics (dactinomycin, doxorubicin, epirubicin, fludarabine and bleomycin). Any chemotherapeutic agent being used to treat the cancer of interest can be co-administered in a combination therapy regime with the PD-1 variants.

For infections, the PD-1 variant can be used alone, or in combination with cytokine therapy, such as the administration of interferons, GM-CSF, G-CSF, IL-2 and the like.

F. Methods of Monitoring Treatment Efficacy

A variety of methods can be employed in determining efficacy of therapeutic treatments with the PD-1 variant polypeptides described herein. Generally, efficacy is the capacity to produce an effect without significant toxicity. Efficacy indicates that the therapy provides therapeutic effects for a given intervention (examples of interventions can include by are not limited to administration of a pharmaceutical formulation, employment of a medical device, or employment of a surgical procedure). Efficacy can be measured by comparing treated to untreated individuals or by comparing the same individual before and after treatment. Efficacy of a treatment can be determined using a variety of methods, including pharmacological studies, diagnostic studies, predictive studies and prognostic studies. Examples of indicators of efficacy include but are not limited to inhibition of tumor cell growth and promotion of tumor cell death.

The efficacy of an anti-cancer treatment can be assessed by a variety of methods known in the art. The PD-1 variant polypeptides can be screened for therapeutic efficacy in animal models in comparison with untreated or placebo controls. The PD-1 variant polypeptides identified by such screens can be then analyzed for the capacity to induce tumor cell death or enhanced immune system activation. For example, multiple dilutions of the PD-1 variant polypeptide can be tested on tumor cell lines in culture and standard methods for examining cell death or inhibition of cellular growth can be employed. See, e.g., Maniatis, et al., *Molecular Cloning: A Laboratory Manual*, Cold Spring Harbor Lab., New York, 1982; Ausubel, et al. Editor, *Current Protocols in Molecular Biology*, USA, 1984-2008; and Ausubel, et al. Editor, *Current Protocols in Molecular Biology*, USA, 1984-2008; Bonifacino, et al., Editor, *Current Protocols in Cell Biology, USA,* 2010; all of which are incorporated herein by reference in their entirety.

A variety of methods can be used to monitor both therapeutic treatment for symptomatic patients. For cancer, monitoring methods can entail determining a baseline value of a tumor burden in a patient before administering a dosage of the PD-1 variant polypeptide, and comparing this with a value for the tumor burden after treatment, respectively. With respect to the PD-1 variant polypeptide therapies, a significant decrease (i.e., greater than the typical margin of experimental error in repeat measurements of the same sample, expressed as one standard deviation from the mean of such measurements) in value of the tumor burden signals a positive treatment outcome (i.e., that administration of the PD-1 variant has elicited an immune response and/or has blocked or inhibited, or reduced progression of tumor growth and/or metastasis). In some embodiments, treatment with the PD-1 variant polypeptide is considered to be efficacious if the tumor burden in the subject being treated is reduced by at least about 10%, for example, by at least about 20%, 30%, 40% or 50%, or by completely eliminating the tumor burden, e.g., comparing tumor burden before and after treatment in the subject. Similarly, for infection, treatment with the PD-1 variant polypeptide is considered to be efficacious if the infection in the subject being treated is reduced by at least about 10%, for example, by at least about 20%, 30%, 40% or 50%, or by completely eliminated as determined by, e.g., comparing the infection before and after treatment in the subject

IV. EXAMPLES

The following examples are offered to illustrate, but not to limit, the claimed invention.

Example 1

Engineering PD-1 Variants With High Affinity to PD-1 Ligands

This example illustrates the use of combinatorial and rational engineering methods to increase the binding affinity of PD-1 variants to PD-1 ligands PD-L1 and/or PD-L2. The engineered PD-1 variants provided in Table 1 have a high affinity for PD-L1 and/or PD-L2. Thus, the PD-1 variants can sequester the PD-1 ligand(s) and reduce or diminish endogenous PD-1 signaling in immune cells including T cells. The engineered PD-1 variants described herein have substantially higher binding affinity for the PD-1 ligand(s) compared to wild-type PD-1. This example describes experiments used to engineer a series of mutants based on the extracellular domain of the human PD-1 polypeptide.

A mutant library was created by performing error-prone PCR on an extracellular domain fragment of wild-type PD-1 using standard molecular biology techniques. The library was expressed using yeast surface display and screened by fluorescence-activated cell sorting (FACS) to isolate mutants that exhibit enhanced binding affinity to one or more PD-1 ligands. In the library screening, the mutant protein library was subjected to multiple rounds of sorting such that each successive round reduced the size of the library and concurrently enriched for proteins with high binding affinity to PD-L1 and/or PD-L2.

Firstly, DNA encoding human PD-1 (UniProt No. Q15116) from amino acids N33 to E150 (Asn at position 33 to Glu at position 150) was cloned into a modified version of the pCT yeast display plasmid (pSJK) in which PD-1 was tethered to the display construct through its C-terminus. Typically in the pCT plasmid, proteins are tethered via their N-terminus. However, since the PD-1/PD-L1 interaction occurs at the N-terminus of the receptor, the pSJK construct was constructed such that PD-1 could be displayed through its C-terminus. A single C93S point mutation was also made in the PD-1 coding sequence to remove an unpaired cysteine residue.

Next, an error-prone library was created using PD-1 DNA as a template, and mutations were introduced using low-fidelity Taq polymerase and the nucleotide analogs 8-ox-dGTP and dPTP. To obtain a range of mutation frequencies, six separate error-prone PCR reactions were performed in which the number of cycles and analog concentrations were varied. For example, the following reactions were performed: eight cycles (200 μM), twelve cycles (2 μM, 20 μM or 200 μM), and eighteen cycles (2 μM or 20 μM). The products from these reactions were amplified using forward and reverse primers each with 50 base-pair homology to the flanking regions of pSJK. Amplified DNA was purified using gel electrophoresis, and the pSJK plasmid was digested with BamHI and NheI. Purified mutant PD-1 DNA and linearized plasmid were electroporated in a 3:1 ratio by weight into EBY100 yeast, where the library was assembled in vivo through homologous recombination. The final library size was estimated to be $3.3 \times 10^8$ by dilution plating.

Yeast displaying high-affinity PD-1 variants were isolated from the library using FACS. The library was progressively enriched for high binding clones over five rounds of equilibrium binding sorts. In these sorts, yeast were incubated at room temperature in phosphate-buffered saline with 1 mg/ml BSA (PBSA) and with the following nominal concentrations of PD-L1-Fc: for sort 1, 250 nM; sort 2, 20 nM; sort 3, 1 nM; sort 4, 0.1 nM; sort 5, 0.1 nM. PD-L1 Fc refers to a human PD-L1-Fc chimeric protein. This recombinant protein contains the extracellular domain of human PD-L1 fused to the Fc region of human IgG1 at the C-terminus. After incubation with PD-L1-Fc, yeast were pelleted, washed, and resuspended in PBSA with chicken anti-cMYC for 1 hour at 4° C. After primary antibody incubation, yeast were once again washed and secondary labeling was performed on ice for 30 minutes using PBSA with goat anti-chicken Alexa Fluor 555 and goat anti-human IgG Alexa Fluor 488. Each sort was conducted such that the 1-3% of clones with the highest PD-L1 binding/cMyc expression ration were selected, thereby enriching the library for clones with the highest affinity. In the first round, $1 \times 10^8$ cells were screened, and in subsequent rounds a minimum of ten-fold the number of clones collected in the prior sort round were screened to ensure adequate sampling of diversity.

Following flow cytometry analysis of sort round 5, plasmid DNA was recovered using a Zymoprep kit, transformed into Top10 cells, and isolated using a plasmid miniprep kit. Sequencing of isolated plasmid DNA was performed.

Analysis of the enriched pool of yeast-displayed PD-1 mutants from sort round 5 was performed using the same reagents and FACS protocols as described for the library sorts. Samples were analyzed using a FACScalibur flow cytometer and data was analyzed using FlowJo software.

Samples of yeast from sorts 5, 3 and 2, as well as wild-type PD-1, were all analyzed under identical conditions to determine the relative improvement in binding affinity to PD-L1. In FIG. 1 the amount of binding to PD-L1 is displayed on the y-axis, while expression on the cell surface is on the x-axis. PD-L1 binding to the yeast-displayed library was enriched over wild-type PD-1 as the sort rounds progressed. After five rounds of sorting, the PD-1 library was significantly enriched for variants that possessed improved binding to PD-L1 (e.g., PD-L1-Fc) with respect to wild-type. Exemplary PD-1 variants are provided in FIG. 1 and Table 1.

Sequencing of these PD-1 mutants identified several mutations within the extracellular domain that conferred enhanced affinity towards PD-L1. Table 1 (above) shows unique amino acid mutations within the sequence of the PD-1 variants identified after five rounds of sorting. In this table, the residue number in the top row indicates the amino acid residue in wild-type PD-1 polypeptide. The second row indicates the residue found in wild-type PD-1 at a given position. In subsequent rows, amino acid mutations present in the given mutant are specified. Absence of an amino acid for a particular residue within a mutant (e.g. a blank space or a blank cell in Table 1) denotes that this amino acid residue is not mutated from the wild-type residue. The standard single letter designation for amino acid residues is used as is well-understood by one who is skilled in the art. The "bp" column represents the number of DNA mismatches. The "AA" column represents number of amino acid mutations. Note that some of the DNA mutations are silent. The total number of times a particular clone showed up is indicated in the right most column.

Described herein is the use of combinatorial and rational protein engineering methodologies to affinity mature soluble variants of an extracellular domain fragment of PD-1 that possess enhanced affinity for PD-1 ligands such as PD-L1 and/or PD-L2. These mutants can be used as effective antagonists of the PD-1 signaling pathway by binding to and blocking the active binding site of PD-1 ligands to their receptor.

Example 2

Second Generation Screening for Engineering PD-1 Variants With High Affinity to PD-1 Ligands Similar to the screen described in Example 1, a second generation screen was performed. The screen combined the beneficial mutations identified in the first generation screen, and to simultaneously removed deleterious and neutral mutations from the mutant pool. In order to do this, a round of DNA shuffling was performed using the enriched pool of mutants from the first screen (e.g., the screen described in Example 1) as the input material for the shuffling.

Plasmid DNA was recovered from the pool of enriched PD-1 mutants after five rounds of sorting of the original library as described in Example 1. DNA recovery was performed using a Zymoprep kit. The recovered plasmid was used as template for a PCR reaction in order to amplify the insert encoding the PD-1 mutants. Additionally, an insert encoding the single point mutant A132V was similarly amplified. PCR products of each were purified by gel electrophoresis, after which 1.5 μg of A132V insert and 6 μg of library insert were mixed. The combined 7.5 μg of DNA was subjected to DNase digestion for 3 minutes at 15° C. in the following reaction: 1 unit DNAse I in 100 μL of 50 mM Tris-HC1 pH 7.5 and 10 mM $MgCl_2$. The digested DNA was then assembled without amplification primers by PCR. Without additional purification, the assembled DNA was used as template for a final PCR reaction. Amplification primers with 50 base pair homology to the yeast display plasmid were used in the final reaction to amplify full length shuffled inserts. Properly assembled and amplified insert DNA was purified by gel electrophoresis.

Purified shuffled DNA and pSJK plasmid linearized with BamHI and NheI were electroporated in a 3:1 ration by weight into EBY100 yeast, where the library was assembled in vivo through homologous recombination. The final library size was estimated to be 2.2×10⁸ by dilution plating.

Yeast displaying high-affinity PD-1 variants were isolated from the second generation library using FACS. The library was progressively enriched for high binding clones over six rounds. For sort rounds 1-3, equilibrium binding sorts were used in which yeast were incubated at room temperature in phosphate-buffered saline with 1 mg/nil BSA (PBSA) and with the following nominal concentrations of soluble PD-L1-Fe or soluble PD-L1: for sort 1, 100 pM PD-L1-Fe; sort 2, 2 nM PD-L1; sort 3, 100 pM PD-L1. After incubation with PD-L1-Fc or PD-L1, yeast were pelleted, washed, and resuspended in PBSA with chicken anti-cMYC for 1 hour at 4° C. After primary antibody incubation, yeast were once again washed and secondary labeling was performed on ice for 30 minutes using PBSA with goat anti-chicken Alexa Fluor 555 and goat anti-human IgG Alexa Fluor 488 or anti-HIS Dylight 488 as appropriate.

For sort rounds 4-6, kinetic off-rate sorts were performed in which yeast were incubated with 5 nM PD-L1 for 2 h at room temperature, after which yeast were washed twice with PBSA to remove any unbound PD-L1. After washing, yeast were resuspended in PBSA containing a ~100 fold molar excess of soluble PD-L1-Fc. The length of the off-rate steps for each sort are as followed: sort 4, 2 h; sort 5, 6 h; sort 6, either 8 h or 12 h. Following the indicated time, yeast were labeled for sorting as previously described.

Each sort was conducted such that the 1-3% of clones with the highest PD-L1 binding/cMyc expression ration were selected, thereby enriching the library for clones with the highest affinity. In the first round, 1×10⁸ cells were screened, and in subsequent rounds a minimum of ten-fold the number of clones collected in the prior sort round were screened to ensure adequate sampling of diversity.

Plasmid DNA was recovered after each sort round using a Zymoprep kit, transformed into Top10 cells, and isolated using a plasmid miniprep kit. Sequencing of isolated plasmid DNA was performed.

Analysis of the enriched pool of yeast-displayed PD-1 mutants from sort rounds 5 and 6 was performed using the same reagents and FACS protocols as described for the library sorts. Samples were analyzed using a FACScalibur flow cytometer and data was analyzed using FlowJo software.

After six rounds of sorting the second generation shuffled PD-1 library, a pool of enriched clones remained that bound to PD-L1 with a higher affinity than wild-type PD-1. Clones from the sort 5 and 6 products were chosen at random and together with wild-type PD-1 were tested for their ability to bind to PD-L1 Fc when displayed on the yeast cell surface. 27 unique clones were identified from 41 random sequences analyzed from the sort 5 and sort 6 library pools. Such remaining diversity after extensive sorting suggests that the beneficial binding properties of the remaining clones are mediated by a core set of common "key" mutations. Exemplary clones that contain the core set of consensus mutations are shown in Table 2. These clones contained the amino acid substitutions provided in Table 2 as well as a C93S substitution.

Yeast expressing individual PD-1 variants (e.g., yeast displayed PD-1 variant polypeptides) were incubated with soluble PD-L1 Fc at 5 nM or 0.5 nM. Binding was allowed to proceed for 3 hours at room temperature at which time yeast were pelleted, washed twice to remove unbound PD-L1-Fc, and stained with a fluorescently labeled secondary antibody to detect the Fc of bound PD-L1. Secondary labeling was performed for 30 minutes on ice, after which yeast were pelleted and washed as described. Yeast samples were then analyzed on a flow cytometer to quantify PD-L1-Fc binding.

All of the randomly chosen engineered clones bound strongly to PD-L1-Fc when tested at both concentrations, while no binding was observed with wild-type PD-1. The clones identified in the second generation screen have enhanced binding to PD-L1 compared to those clones identified in the first generation screen.

Figure 2:
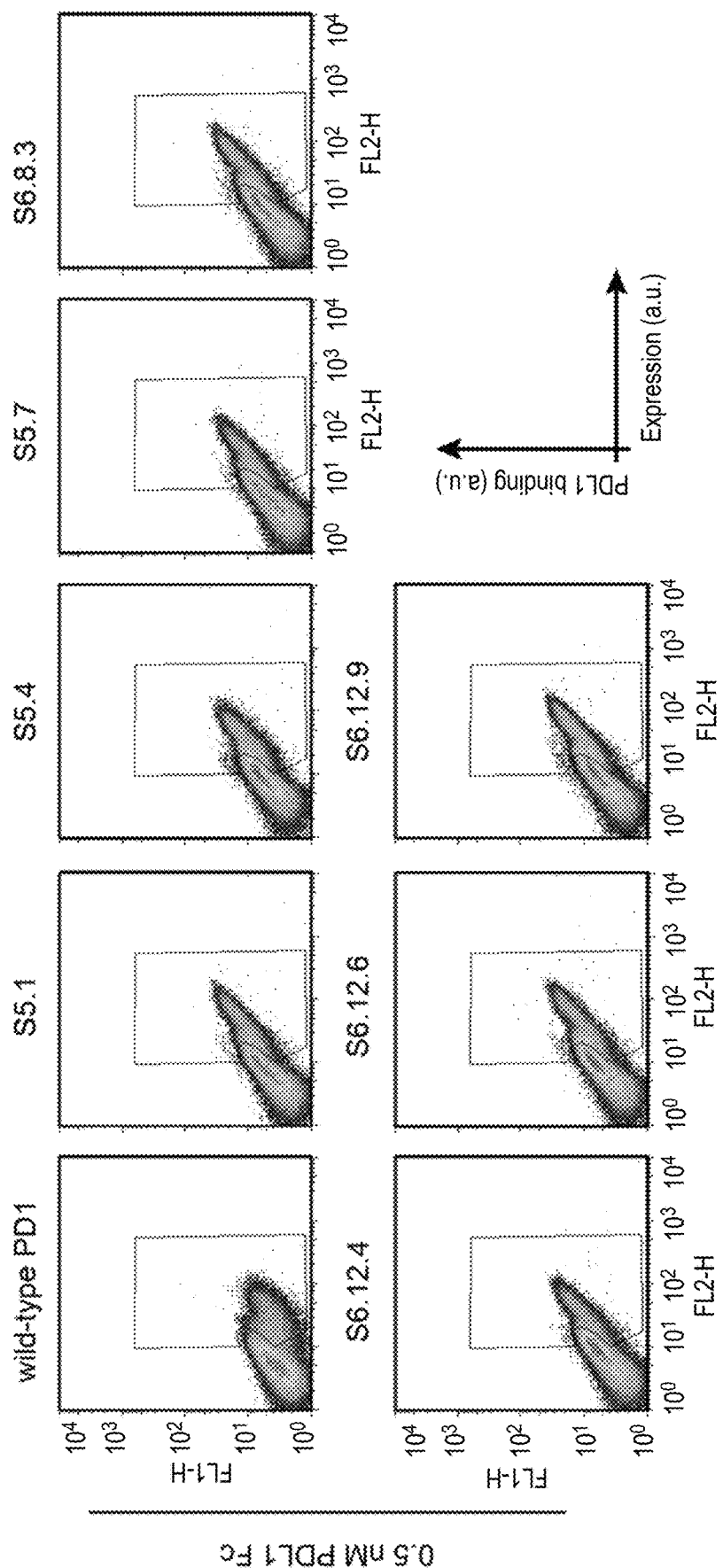
FIG. 2 provides FACS analysis of yeast clones expressing PD-1 variants displayed in the cell surface and bound to PD-L1-Fc chimeric proteins. In this binding assay 0.5 mM PD-L1-Fc was used. The graphs show PD-L1 binding (a. u.) on the y-axis and PD-1 variant expression on the X-axis.
Figure 3:
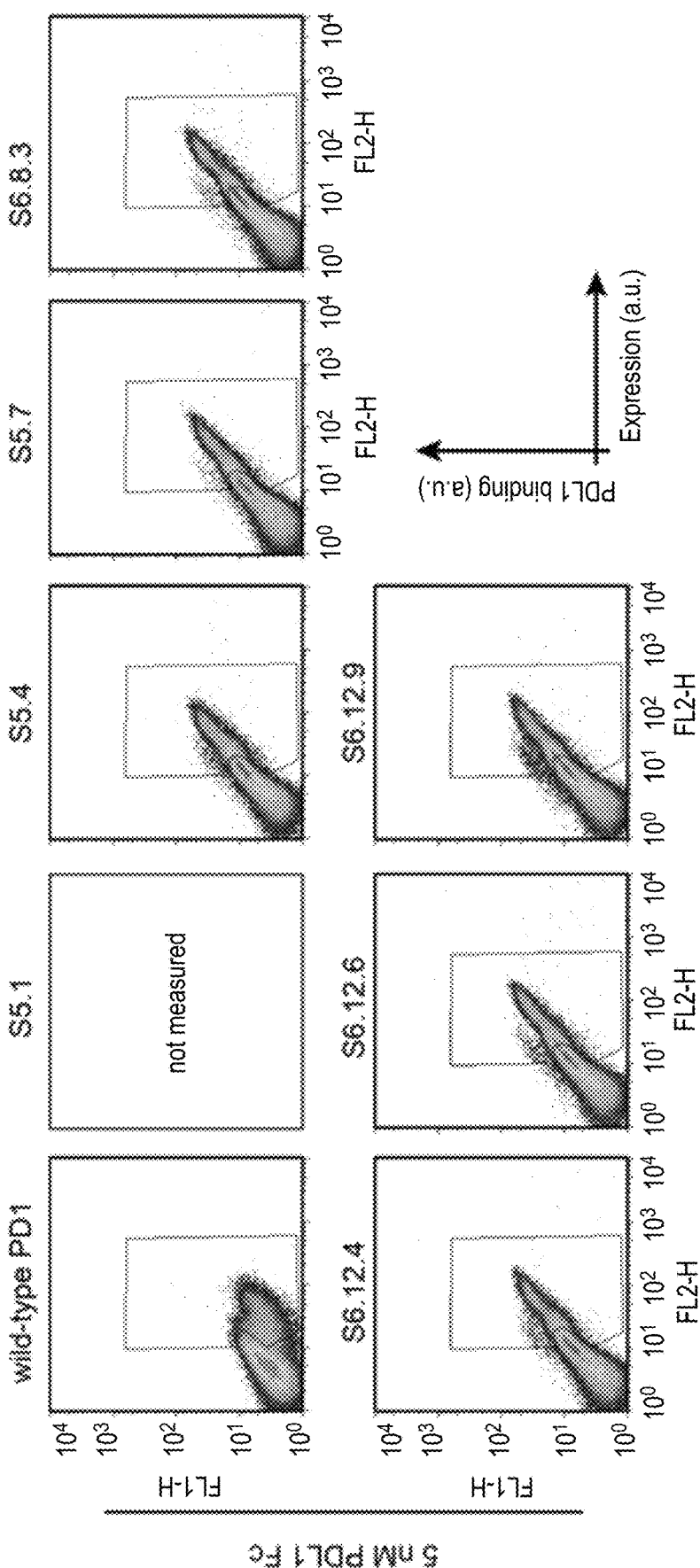
FIG. 3 provides FACS analysis of yeast clones expressing PD-1 variants displayed in the cell surface and bound to PD-L1-Fc chimeric proteins. In this binding assay 5 nM PD-L1-Fc was used. The graphs show PD-L1 binding (a. u.) on the y-axis and PD-1 variant expression on the X-axis.
Figure 4:
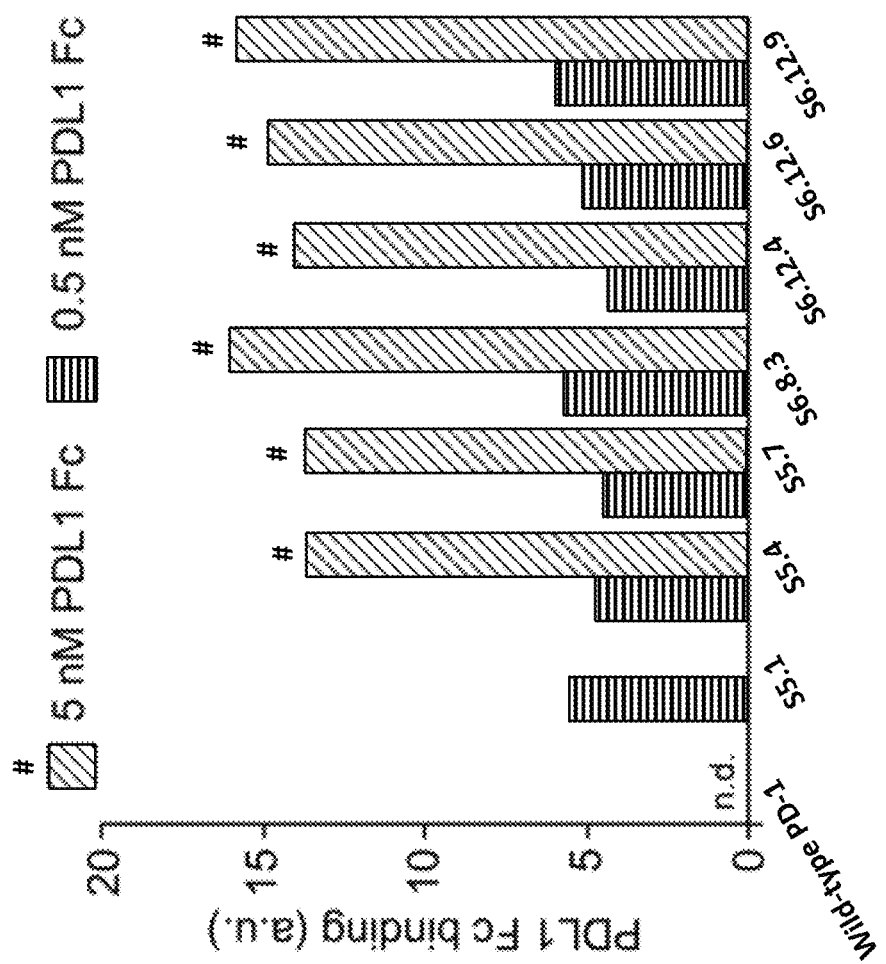
FIG. 4 presents the FACS data of FIGS. 2 and 3 as a bar graph.

FIG. 2 shows that all the clones from the second generation screen bound strongly to PD-L1, specifically, the soluble PD-L1-Fc chimeric protein at a concentration of 0.5 nM. FIG. 3 shows clones from the second generation screening bound strongly to PD-L1, in particular, the soluble PD-L1-Fc chimeric protein at a concentration of 5 nM. Clone S5.1 was not tested with this concentration of PD-L1-Fc. FIG. 4 provides a graph of the FACS data.

This example provides PD-1 variant polypeptides that contain amino acid substitutions relative to wild-type PD-1. These variant polypeptides have amino acid substitutions at consensus positions relative to the wild-type sequence, such as at positions S87, P89, N116, G124, S127, A132, and A140.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A composition comprising a PD-1 variant polypeptide, wherein the variant polypeptide lacks the PD-1 transmembrane and intracellular domains, wherein the variant polypeptide comprises an amino acid substitution of A140V as compared to SEQ ID NO:1, and wherein the variant polypeptide provides enhanced binding to human PD-L1 as compared to SEQ ID NO:1.

2. A composition comprising a PD-1 variant polypeptide, wherein the variant polypeptide lacks the PD-1 transmembrane and intracellular domains, wherein the variant polypeptide comprises an amino acid substitution of A140V as compared to SEQ ID NO:1, wherein the variant polypeptide provides enhanced binding to human PD-L1 as compared to SEQ ID NO:1, and wherein the variant polypeptide has at least 97% sequence identity to the extracellular domain of SEQ ID NO:1.

3. A nucleic acid encoding the PD-1 variant polypeptide of claim 1.

4. A nucleic acid encoding the PD-1 variant polypeptide of claim 2.

5. An expression vector comprising the nucleic acid of claim 3.

6. An expression vector comprising the nucleic acid of claim 4.

7. A host cell comprising the nucleic acid of claim 3.

8. A host cell comprising the expression vector of claim 5.

9. A host cell comprising the nucleic acid of claim 4.

10. A host cell comprising the expression vector of claim 6.

11. A method of making a PD-1 variant polypeptide comprising: a) culturing the host cell of claim 7 under conditions wherein the PD-1 variant polypeptide is expressed; and b) recovering the PD-1 variant polypeptide.

12. A method of making a PD-1 variant polypeptide comprising: a) culturing the host cell of claim 8 under conditions wherein the PD-1 variant polypeptide is expressed; and b) recovering the PD-1 variant polypeptide.

13. A method of making a PD-1 variant polypeptide comprising: a) culturing the host cell of claim 9 under conditions wherein the PD-1 variant polypeptide is expressed; and b) recovering the PD-1 variant polypeptide.

14. A method of making a PD-1 variant polypeptide comprising: a) culturing the host cell of claim 10 under conditions wherein the PD-1 variant polypeptide is expressed; and b) recovering the PD-1 variant polypeptide.

15. A pharmaceutical composition comprising a therapeutically effective amount of the PD-1 variant polypeptide of claim 1 or a pharmaceutically acceptable salt thereof.

16. The pharmaceutical composition of claim 15, further comprising a pharmaceutically acceptable carrier or a cytotoxic agent.

17. The pharmaceutical composition of claim 15, further comprising a pharmaceutically acceptable carrier and a cytotoxic agent.

18. A pharmaceutical composition comprising a therapeutically effective amount of the PD-1 variant polypeptide of claim 2 or a pharmaceutically acceptable salt thereof.

19. The pharmaceutical composition of claim 18, further comprising a pharmaceutically acceptable carrier or a cytotoxic agent.

20. The pharmaceutical composition of claim 18, further comprising a pharmaceutically acceptable carrier and a cytotoxic agent.

* * * * *

SEQUENCE LISTING

<160> NUMBER OF SEQ ID NOS: 29

<210> SEQ ID NO 1
<211> LENGTH: 288
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

-continued

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 2
<211> LENGTH: 118
<212> TYPE: PRT
<213> ORGANISM: Artificial Sequence
<220> FEATURE:
<223> OTHER INFORMATION: synthetic wild-type human programmed cell death
      1 receptor (PD-1) polypeptide fragment

<400> SEQUENCE: 2

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Ser Gln Pro Gly Gln Asp Cys Arg Phe Arg
    50                  55                  60

Val Thr Gln Leu Pro Asn Gly Arg Asp Phe His Met Ser Val Val Arg
65                  70                  75                  80

Ala Arg Arg Asn Asp Ser Gly Thr Tyr Leu Cys Gly Ala Ile Ser Leu
                85                  90                  95

Ala Pro Lys Ala Gln Ile Lys Glu Ser Leu Arg Ala Glu Leu Arg Val

Thr Glu Arg Arg Ala Glu
        115

<210> SEQ ID NO 3
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 3

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Ser Gln Pro Gly Gln Asp Ser Arg Phe Arg
    50                  55                  60

Val Thr Gln Leu Pro Asn Gly Arg Asp Phe His Met Ser Val Val Arg
65                  70                  75                  80

Ala Arg Arg Asn Asp Ser Gly Thr Tyr Leu Cys Gly Ala Ile Ser Leu
                85                  90                  95

Ala Pro Lys Val Gln Ile Lys Glu Ser Leu Arg Ala Glu Leu Arg Val
            100                 105                 110

Thr Glu Arg Arg Ala Glu
        115

<210> SEQ ID NO 4
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 4

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Gly Gln Pro Gly Gln Asp Ser Arg Phe Arg
    50                  55                  60

Val Ile Gln Leu Pro Asn Gly Arg Asp Phe His Met Ser Val Val Arg
65                  70                  75                  80

Ala Arg Arg Asn Asp Ser Gly Thr Tyr Leu Cys Gly Ala Ile Ser Leu
                85                  90                  95

Ala Pro Lys Val Gln Ile Lys Glu Ser Leu Arg Ala Glu Leu Arg Val
            100                 105                 110

Thr Glu Arg Arg Ala Glu
        115

<210> SEQ ID NO 5
<211> LENGTH: 118
<212> TYPE: PRT
<213> ORGANISM: Artificial Sequence
<220> FEATURE:

<223> OTHER INFORMATION: synthetic PD-1 variant polypeptide

<400> SEQUENCE: 5

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Ser Gln Pro Gly Gln Asp Ser Arg Phe Arg
    50                  55                  60

Val Thr Gln Leu Pro Asn Gly Arg Asp Phe His Met Ser Val Val Arg
65                  70                  75                  80

Ala Arg Arg Ser Asp Ser Gly Thr Tyr Leu Cys Gly Ala Ile Ser Leu
            85                  90                  95

Ala Pro Lys Val Gln Ile Lys Glu Ser Leu Arg Ala Glu Leu Arg Val
            100                 105                 110

Ile Glu Arg Arg Ala Glu
        115

<210> SEQ ID NO 6
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 6

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Val Ser Pro Ser Asn Gln Thr Asp Lys Leu Ala
        35                  40                  45

Ala Phe Pro Glu Asp Arg Ser Arg Pro Gly Gln Asp Ser Arg Phe Arg
    50                  55                  60

Val Thr Arg Leu Pro Asn Gly Arg Asp Phe His Met Ser Val Val Gly
65                  70                  75                  80

Ala Arg Arg Ser Asp Ser Gly Thr Tyr Leu Cys Gly Ala Ile Ser Leu
            85                  90                  95

Ala Pro Lys Val Gln Ile Lys Glu Ser Leu Arg Ala Glu Leu Arg Val
            100                 105                 110

Thr Glu Arg Arg Ala Glu
        115

<210> SEQ ID NO 7
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 7

Asn Pro Pro Thr Phe Ser Pro Ala Leu Leu Val Val Thr Glu Gly Asp
1               5                   10                  15

Asn Ala Thr Phe Thr Cys Ser Phe Ser Asn Ala Ser Glu Ser Phe Val
            20                  25                  30

Leu Asn Trp Tyr Arg Met Ser Pro Ser Asp Gln Thr Asp Lys Leu Ala

```
                35                  40                  45
Ala Phe Pro Glu Asp Arg Gly Gln Leu Gly Gln Asp Ser Arg Phe Arg
        50                  55                  60
Val Thr Gln Leu Pro Asn Gly Arg Asp Phe His Met Ser Val Val Arg
65                  70                  75                  80
Ala Arg Arg Asn Asp Ser Gly Thr Tyr Leu Cys Gly Ala Ile Ser Leu
                85                  90                  95
Ala Pro Lys Ile Gln Ile Lys Glu Ser Leu Arg Ala Glu Leu Arg Val
                100                 105                 110
Thr Glu Arg Arg Ala Glu
        115
```

<210> SEQ ID NO 8
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 8

```
Asn Pro Pro Thr Phe Ser Pro Ala Leu Leu Val Val Thr Glu Gly Asp
1               5                   10                  15
Asn Ala Thr Phe Thr Cys Ser Phe Ser Asn Thr Ser Glu Ser Phe Val
                20                  25                  30
Leu Asn Trp Tyr Arg Met Ser Pro Ser Asn Gln Thr Asp Lys Leu Ala
                35                  40                  45
Ala Phe Pro Glu Asp Arg Ser Gln Pro Gly Gln Asp Ser Arg Phe Arg
        50                  55                  60
Val Thr Gln Leu Pro Asn Gly Arg Asp Phe Arg Met Ser Val Val Arg
65                  70                  75                  80
Ala Arg Arg Ser Asp Ser Gly Thr Tyr Leu Cys Ser Ala Ile Ser Leu
                85                  90                  95
Ala Pro Lys Val Gln Ile Lys Glu Ser Leu Arg Ala Glu Leu Arg Val
                100                 105                 110
Thr Glu Arg Arg Ala Glu
        115
```

<210> SEQ ID NO 9
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 9

```
Asn Pro Pro Thr Phe Ser Pro Ala Leu Leu Val Val Thr Glu Gly Asp
1               5                   10                  15
Asn Ala Thr Phe Thr Cys Ser Phe Ser Asn Thr Ser Glu Ser Phe Val
                20                  25                  30
Leu Asn Trp Tyr Arg Met Ser Pro Ser Asn Gln Thr Asp Lys Leu Ala
                35                  40                  45
Ala Phe Pro Glu Asp Arg Ser Gln Pro Gly Gln Asp Ser Arg Phe Arg
        50                  55                  60
Val Thr Gln Leu Pro Asn Gly Arg Asp Phe His Met Ser Val Val Arg
65                  70                  75                  80
Ala Arg Arg Asn Asp Ser Gly Thr Tyr Leu Cys Gly Ala Ile Ser Leu
                85                  90                  95
```

```
Ala Pro Lys Val Gln Ile Lys Glu Ser Leu Arg Val Glu Leu Arg Val
            100                 105                 110

Thr Glu Arg Arg Ala Glu
        115

<210> SEQ ID NO 10
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 10

Asp Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Ser Gln Pro Gly Gln Asp Ser Arg Phe Arg
    50                  55                  60

Val Thr Gln Leu Pro Asn Gly Arg Asp Phe His Met Ser Val Val Arg
65                  70                  75                  80

Ala Arg Arg Asp Asp Ser Gly Thr Tyr Leu Cys Gly Ala Ile Ser Leu
                85                  90                  95

Ala Pro Lys Ile Gln Ile Lys Glu Ser Leu Arg Ala Glu Leu Arg Val
            100                 105                 110

Thr Glu Arg Arg Ala Glu
        115

<210> SEQ ID NO 11
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 11

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Ser Gln Pro Gly Gln Asp Ser Arg Phe Arg
    50                  55                  60

Val Thr Gln Leu Pro Asn Gly Arg Asp Phe His Met Ser Val Val Arg
65                  70                  75                  80

Ala Arg Gly Asp Asp Ser Gly Thr Tyr Leu Cys Gly Ala Ile Ser Leu
                85                  90                  95

Ala Pro Lys Val Gln Ile Lys Glu Ser Leu Arg Val Glu Leu Arg Val
            100                 105                 110

Thr Glu Arg Arg Ala Glu
        115

<210> SEQ ID NO 12
<211> LENGTH: 118
<212> TYPE: PRT
<213> ORGANISM: Artificial Sequence
```

```
<220> FEATURE:
<223> OTHER INFORMATION: synthetic PD-1 variant polypeptide

<400> SEQUENCE: 12

Asp Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Ser Gln Pro Gly Gln Asp Ser Arg Phe Arg
    50                  55                  60

Val Thr Gln Leu Pro Asn Gly Arg Asp Phe His Met Ser Val Val Arg
65                  70                  75                  80

Ala Arg Arg Asn Asp Ser Gly Thr Tyr Leu Cys Gly Ala Ile Leu Leu
                85                  90                  95

Ala Pro Arg Ile Gln Ile Arg Glu Ser Leu Gly Ala Glu Leu Arg Val
            100                 105                 110

Thr Glu Lys Gly Ala Glu
        115

<210> SEQ ID NO 13
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 13

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Ser Gln Leu Gly Gln Asp Ser Arg Phe Arg
    50                  55                  60

Val Thr Gln Leu Pro Asn Gly Arg Asp Phe His Met Ser Val Val Arg
65                  70                  75                  80

Ala Arg Arg Asn Asp Ser Gly Thr Tyr Leu Cys Gly Ala Ile Ser Leu
                85                  90                  95

Ala Pro Lys Val Gln Ile Arg Glu Ser Leu Arg Val Gly Leu Arg Val
            100                 105                 110

Thr Glu Arg Arg Ala Glu
        115

<210> SEQ ID NO 14
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 14

Asn Pro Pro Thr Phe Ser Pro Ala Leu Leu Val Val Thr Glu Gly Asp
1               5                   10                  15

Ser Ala Thr Phe Thr Cys Ser Phe Ser Asn Thr Ser Glu Ser Phe Val
            20                  25                  30
```

Leu Asn Trp Tyr Arg Met Ser Pro Ser Asn Gln Ala Asp Lys Leu Ala
            35                  40                  45

Ala Phe Pro Glu Asp Arg Ser Gln Pro Gly Gln Asp Ser Arg Phe Arg
 50                  55                  60

Val Thr Gln Leu Pro Asn Gly Arg Asp Phe His Met Ser Val Val Gly
 65                  70                  75                  80

Ala Arg Arg Ser Asp Ser Gly Thr Tyr Leu Cys Ser Ala Ile Ser Leu
                85                  90                  95

Ala Pro Lys Val Gln Ile Arg Glu Ser Leu Arg Ala Glu Leu Arg Val
                100                 105                 110

Ala Glu Arg Arg Ala Glu
            115

<210> SEQ ID NO 15
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 15

Asn Pro Pro Thr Phe Ser Pro Ala Leu Leu Val Val Thr Glu Gly Asp
 1               5                  10                  15

Asn Ala Thr Phe Thr Cys Ser Phe Ser Asn Thr Ser Glu Ser Phe Val
                20                  25                  30

Leu Asn Trp Tyr Arg Met Ser Pro Ser Asp Gln Thr Asp Lys Leu Ala
            35                  40                  45

Ala Phe Pro Glu Asp Arg Ser Arg Pro Gly Gln Asp Ser Arg Phe Arg
 50                  55                  60

Val Thr Gln Leu Pro Asn Gly Arg Asp Phe His Met Ser Val Val Gly
 65                  70                  75                  80

Ala Arg Arg Asn Asp Ser Gly Thr Tyr Leu Cys Gly Ala Ile Ser Leu
                85                  90                  95

Ala Pro Lys Val Gln Ile Arg Glu Ser Leu Arg Ala Glu Leu Arg Val
                100                 105                 110

Thr Glu Arg Arg Ala Glu
            115

<210> SEQ ID NO 16
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 16

Asn Pro Pro Thr Leu Ser Pro Ala Leu Leu Val Val Thr Glu Gly Asp
 1               5                  10                  15

Asn Ala Thr Phe Thr Cys Ser Phe Ser Asn Thr Ser Glu Ser Phe Val
                20                  25                  30

Leu Asn Trp Tyr Arg Met Ser Pro Ser Asn Gln Thr Asp Lys Leu Ala
            35                  40                  45

Ala Phe Pro Glu Asp Arg Ser Gln Pro Gly Gln Asp Ser Arg Phe Arg
 50                  55                  60

Val Thr Gln Leu Pro Asn Gly Arg Asp Phe His Met Ser Val Val Arg
 65                  70                  75                  80

Ala Arg Arg Asp Asp Ser Gly Thr Tyr Leu Cys Gly Ala Ile Ser Leu
                85                  90                  95

```
Ala Pro Lys Val Gln Ile Lys Glu Ser Leu Arg Ala Glu Leu Arg Val
            100                 105                 110

Thr Glu Arg Arg Ala Glu
        115

<210> SEQ ID NO 17
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 17

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Ser Gln Pro Gly Gln Asp Ser Arg Phe Arg
    50                  55                  60

Val Thr Gln Leu Pro Asn Gly Arg Asp Phe His Met Ser Val Val Gly
65                  70                  75                  80

Ala Arg Arg Asn Asp Ser Gly Thr Tyr Leu Cys Gly Ala Ile Ser Leu
                85                  90                  95

Ala Pro Lys Ile Gln Ile Lys Glu Ser Leu Arg Ala Glu Leu Arg Val
            100                 105                 110

Thr Glu Arg Arg Ala Glu
        115

<210> SEQ ID NO 18
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 18

Asn Pro Pro Thr Phe Ser Pro Ala Leu Leu Val Val Ala Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Ser Gln Pro Gly Gln Asp Arg Arg Phe Arg
    50                  55                  60

Val Thr Gln Leu Pro Ser Gly Arg Asp Phe His Met Ser Val Val Arg
65                  70                  75                  80

Ala Arg Arg Asn Asp Ser Gly Thr Tyr Leu Cys Gly Ala Ile Phe Leu
                85                  90                  95

Ala Pro Arg Ile Gln Ile Lys Glu Ser Leu Arg Ala Glu Leu Arg Val
            100                 105                 110

Thr Glu Arg Arg Ala Glu
        115

<210> SEQ ID NO 19
<211> LENGTH: 118
<212> TYPE: PRT
```

<213> ORGANISM: Artificial Sequence
<220> FEATURE:
<223> OTHER INFORMATION: synthetic PD-1 variant polypeptide

<400> SEQUENCE: 19

```
Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Ser Gln Thr Asp Lys Leu Ala
        35                  40                  45

Ala Phe Pro Glu Asp Arg Ser Gln Pro Gly Gln Asp Ser Arg Phe Arg
    50                  55                  60

Val Thr Gln Leu Pro Asn Gly Arg Asp Phe His Met Ser Val Val Arg
65                  70                  75                  80

Ala Arg Arg Asn Asp Ser Gly Thr Tyr Leu Cys Gly Ala Ile Ser Leu
                85                  90                  95

Ala Pro Lys Val Gln Ile Lys Glu Ser Leu Arg Ala Glu Leu Arg Val
            100                 105                 110

Thr Glu Arg Arg Ala Glu
        115
```

<210> SEQ ID NO 20
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 20

```
Ser Pro Pro Thr Leu Ser Pro Ala Leu Leu Val Val Thr Glu Gly Asp
1               5                   10                  15

Asn Val Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Gly Gln Pro Gly Arg Asp Ser Arg Phe Arg
    50                  55                  60

Val Thr Gln Leu Pro Asn Gly Arg Asp Phe His Met Ser Val Val Arg
65                  70                  75                  80

Ala Arg Arg Asn Asp Ser Gly Thr Tyr Leu Cys Gly Ala Ile Ser Leu
                85                  90                  95

Ala Pro Lys Val Gln Ile Lys Glu Ser Leu Arg Ala Glu Leu Arg Val
            100                 105                 110

Thr Glu Arg Arg Ala Glu
        115
```

<210> SEQ ID NO 21
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 21

```
Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30
```

```
Leu Asn Trp Tyr Arg Met Ser Pro Ser Gln Thr Asp Lys Leu Ala
        35                  40                  45

Ala Phe Pro Glu Asp Arg Ser Gln Pro Gly Gln Asp Ser Arg Phe Arg
 50                  55                  60

Val Thr Gln Leu Pro Asn Gly Arg Asp Phe His Met Ser Val Val Arg
 65                  70                  75                  80

Ala Arg Arg Ser Asp Ser Gly Thr Tyr Leu Cys Gly Val Ile Ser Leu
                 85                  90                  95

Ala Pro Lys Val Gln Ile Lys Glu Ser Leu Arg Ala Glu Leu Arg Val
                100                 105                 110

Ile Glu Arg Arg Ala Glu
        115

<210> SEQ ID NO 22
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 22

Asn Pro Pro Thr Phe Ser Pro Ala Leu Leu Val Val Thr Glu Gly Asp
 1               5                  10                  15

Asn Ala Thr Phe Thr Cys Ser Phe Ser Asn Thr Ser Glu Ser Phe Val
                 20                  25                  30

Leu Asn Trp Tyr Arg Met Ser Pro Ser Asn Gln Thr Asp Lys Leu Ala
        35                  40                  45

Ala Phe Pro Glu Asp Arg Gly Gln Leu Gly Gln Asp Ser Arg Phe Arg
 50                  55                  60

Val Thr Gln Leu Pro Asn Gly Arg Asp Phe His Met Ser Val Val Arg
 65                  70                  75                  80

Ala Arg Arg Ser Asp Ser Gly Thr Tyr Leu Cys Ser Ala Ile Val Leu
                 85                  90                  95

Ala Pro Lys Ile Gln Ile Lys Glu Ser Leu Arg Val Glu Leu Arg Val
                100                 105                 110

Thr Glu Arg Arg Ala Glu
        115

<210> SEQ ID NO 23
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 23

Asn Pro Pro Thr Phe Ser Pro Ala Leu Leu Val Val Thr Glu Gly Asp
 1               5                  10                  15

Asn Ala Thr Phe Thr Cys Ser Phe Ser Asn Thr Ser Glu Ser Phe Val
                 20                  25                  30

Leu Asn Trp Tyr Arg Met Ser Pro Ser Asn Gln Thr Asp Lys Leu Ala
        35                  40                  45

Ala Phe Pro Glu Asp Arg Gly Gln Pro Gly Arg Asp Ser Arg Phe Arg
 50                  55                  60

Val Thr Gln Leu Pro Asn Gly Arg Asp Phe Arg Met Ser Val Val Arg
 65                  70                  75                  80

Ala Arg Arg Ser Asp Ser Gly Thr Tyr Leu Cys Ser Ala Ile Leu Leu
```

```
                      85                  90                  95

Ala Pro Lys Ile Gln Ile Lys Glu Ser Leu Gly Ala Glu Leu Arg Val
            100                 105                 110

Thr Glu Lys Gly Ala Glu
        115
```

<210> SEQ ID NO 24
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 24

```
Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Gly Gln Leu Gly Gln Asp Ser Arg Phe Arg
    50                  55                  60

Val Thr Gln Leu Pro Asn Gly Arg Asp Phe His Met Ser Val Val Arg
65                  70                  75                  80

Ala Arg Arg Ser Asp Ser Gly Thr Tyr Leu Cys Ser Ala Ile Leu Leu
                85                  90                  95

Ala Pro Lys Ile Gln Ile Lys Glu Ser Leu Arg Val Glu Leu Arg Val
            100                 105                 110

Thr Glu Arg Arg Ala Glu
        115
```

<210> SEQ ID NO 25
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 25

```
Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Gly Gln Leu Gly Gln Ala Ser Arg Phe Arg
    50                  55                  60

Val Thr Gln Leu Pro Asn Gly Arg Asp Phe His Met Ser Val Val Arg
65                  70                  75                  80

Ala Arg Arg Ser Asp Ser Gly Thr Tyr Leu Cys Ser Ala Ile Leu Leu
                85                  90                  95

Ala Pro Arg Ile Gln Ile Arg Glu Ser Leu Arg Val Glu Leu Arg Val
            100                 105                 110

Thr Glu Arg Arg Ala Glu
        115
```

<210> SEQ ID NO 26
<211> LENGTH: 118

```
<212> TYPE: PRT
<213> ORGANISM: Artificial Sequence
<220> FEATURE:
<223> OTHER INFORMATION: synthetic PD-1 variant polypeptide

<400> SEQUENCE: 26

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Gly Gln Ser Gly Gln Gly Ser Arg Phe Gly
    50                  55                  60

Val Thr Arg Leu Pro Asn Gly Arg Asp Phe His Met Ser Val Val Arg
65                  70                  75                  80

Ala Arg Arg Ser Asp Ser Gly Thr Tyr Leu Cys Ser Ala Ile Ser Leu
                85                  90                  95

Ala Pro Lys Val Gln Ile Lys Glu Ser Leu Arg Val Glu Leu Arg Val
            100                 105                 110

Thr Glu Arg Arg Ala Glu
        115

<210> SEQ ID NO 27
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 27

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Ile Ser Pro Ser Asn Gln Thr Asp Lys Leu Ala
        35                  40                  45

Ala Phe Pro Glu Asp Arg Gly Gln Leu Gly Gln Asp Ser Arg Phe Arg
    50                  55                  60

Val Thr Gln Leu Pro Asn Gly Arg Asp Phe His Met Ser Val Val Arg
65                  70                  75                  80

Ala Arg Arg Ser Asp Ser Gly Thr Tyr Leu Cys Ser Ala Ile Leu Leu
                85                  90                  95

Ala Pro Arg Ile Gln Ile Arg Glu Ser Leu Gly Val Glu Leu Arg Val
            100                 105                 110

Thr Glu Lys Arg Ala Glu
        115

<210> SEQ ID NO 28
<211> LENGTH: 118
<212> TYPE: PRT
<213> ORGANISM: Artificial Sequence
<220> FEATURE:
<223> OTHER INFORMATION: synthetic PD-1 variant polypeptide

<400> SEQUENCE: 28

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
```

-continued

```
                    20                  25                  30

Leu Asn Trp Tyr Arg Met Ser Pro Ser Asn Gln Thr Asp Lys Leu Ala
         35                  40                  45

Ala Phe Pro Glu Asp Arg Gly Gln Leu Gly Gln Asp Ser Arg Phe Arg
     50                  55                  60

Val Thr Gln Leu Pro Asn Gly Arg Asp Phe His Met Ser Val Val Arg
 65                  70                  75                  80

Ala Arg Arg Ser Asp Ser Gly Thr Tyr Leu Cys Ser Ala Ile Val Leu
                 85                  90                  95

Ala Pro Arg Ile Gln Ile Lys Glu Ser Leu Arg Val Glu Leu Arg Val
             100                 105                 110

Thr Glu Arg Arg Ala Glu
         115

<210> SEQ ID NO 29
<211> LENGTH: 288
<212> TYPE: PRT
<213> ORGANISM: Artificial Sequence
<220> FEATURE:
<223> OTHER INFORMATION: synthetic PD-1 variant polypeptide
<220> FEATURE:
<221> NAME/KEY: VARIANT
<222> LOCATION: (33)..(33)
<223> OTHER INFORMATION: Xaa may be Asn, Asp or Ser
<220> FEATURE:
<221> NAME/KEY: VARIANT
<222> LOCATION: (37)..(37)
<223> OTHER INFORMATION: Xaa may be Phe or Leu
<220> FEATURE:
<221> NAME/KEY: VARIANT
<222> LOCATION: (45)..(45)
<223> OTHER INFORMATION: Xaa may be Thr or Ala
<220> FEATURE:
<221> NAME/KEY: VARIANT
<222> LOCATION: (49)..(49)
<223> OTHER INFORMATION: Xaa may be Asn or Ser
<220> FEATURE:
<221> NAME/KEY: VARIANT
<222> LOCATION: (50)..(50)
<223> OTHER INFORMATION: Xaa may be Ala or Val
<220> FEATURE:
<221> NAME/KEY: VARIANT
<222> LOCATION: (59)..(59)
<223> OTHER INFORMATION: Xaa may be Thr or Ala
<220> FEATURE:
<221> NAME/KEY: VARIANT
<222> LOCATION: (70)..(70)
<223> OTHER INFORMATION: Xaa may be Met, Val or Ile
<220> FEATURE:
<221> NAME/KEY: VARIANT
<222> LOCATION: (74)..(74)
<223> OTHER INFORMATION: Xaa may be Asn, Asp or Ser
<220> FEATURE:
<221> NAME/KEY: VARIANT
<222> LOCATION: (76)..(76)
<223> OTHER INFORMATION: Xaa may be Thr or Ala
<220> FEATURE:
<221> NAME/KEY: VARIANT
<222> LOCATION: (87)..(87)
<223> OTHER INFORMATION: Xaa may be Ser or Gly
<220> FEATURE:
<221> NAME/KEY: VARIANT
<222> LOCATION: (88)..(88)
<223> OTHER INFORMATION: Xaa may be Gln or Arg
<220> FEATURE:
<221> NAME/KEY: VARIANT
<222> LOCATION: (89)..(89)
<223> OTHER INFORMATION: Xaa may be Pro, Leu or Ser
<220> FEATURE:
<221> NAME/KEY: VARIANT
<222> LOCATION: (91)..(91)
<223> OTHER INFORMATION: Xaa may be Gln or Arg
```

```
<220> FEATURE:
<221> NAME/KEY: VARIANT
<222> LOCATION: (92)..(92)
<223> OTHER INFORMATION: Xaa may be Asp, Ala or Gly
<220> FEATURE:
<221> NAME/KEY: VARIANT
<222> LOCATION: (93)..(93)
<223> OTHER INFORMATION: Xaa may be Cys, Ser or Arg
<220> FEATURE:
<221> NAME/KEY: VARIANT
<222> LOCATION: (96)..(96)
<223> OTHER INFORMATION: Xaa may be Arg or Gly
<220> FEATURE:
<221> NAME/KEY: VARIANT
<222> LOCATION: (98)..(98)
<223> OTHER INFORMATION: Xaa may be Thr or Ile
<220> FEATURE:
<221> NAME/KEY: VARIANT
<222> LOCATION: (99)..(99)
<223> OTHER INFORMATION: Xaa may be Gln, Ala or Arg
<220> FEATURE:
<221> NAME/KEY: VARIANT
<222> LOCATION: (102)..(102)
<223> OTHER INFORMATION: Xaa may be Asn or Ser
<220> FEATURE:
<221> NAME/KEY: VARIANT
<222> LOCATION: (107)..(107)
<223> OTHER INFORMATION: Xaa may be His or Arg
<220> FEATURE:
<221> NAME/KEY: VARIANT
<222> LOCATION: (112)..(112)
<223> OTHER INFORMATION: Xaa may be Arg or Gly
<220> FEATURE:
<221> NAME/KEY: VARIANT
<222> LOCATION: (115)..(115)
<223> OTHER INFORMATION: Xaa may be Arg or Gly
<220> FEATURE:
<221> NAME/KEY: VARIANT
<222> LOCATION: (116)..(116)
<223> OTHER INFORMATION: Xaa may be Asn, Asp or Ser
<220> FEATURE:
<221> NAME/KEY: VARIANT
<222> LOCATION: (124)..(124)
<223> OTHER INFORMATION: Xaa may be Gly or Ser
<220> FEATURE:
<221> NAME/KEY: VARIANT
<222> LOCATION: (125)..(125)
<223> OTHER INFORMATION: Xaa may be Ala or Val
<220> FEATURE:
<221> NAME/KEY: VARIANT
<222> LOCATION: (127)..(127)
<223> OTHER INFORMATION: Xaa may be Ser, Phe, Leu, or Val
<220> FEATURE:
<221> NAME/KEY: VARIANT
<222> LOCATION: (131)..(131)
<223> OTHER INFORMATION: Xaa may be Lys or Arg
<220> FEATURE:
<221> NAME/KEY: VARIANT
<222> LOCATION: (132)..(132)
<223> OTHER INFORMATION: Xaa may be Ala, Ile or Val
<220> FEATURE:
<221> NAME/KEY: VARIANT
<222> LOCATION: (135)..(135)
<223> OTHER INFORMATION: Xaa may be Lys or Arg
<220> FEATURE:
<221> NAME/KEY: VARIANT
<222> LOCATION: (139)..(139)
<223> OTHER INFORMATION: Xaa may be Arg or Gly
<220> FEATURE:
<221> NAME/KEY: VARIANT
<222> LOCATION: (140)..(140)
<223> OTHER INFORMATION: Xaa may be Ala or Val
<220> FEATURE:
<221> NAME/KEY: VARIANT
<222> LOCATION: (145)..(145)
<223> OTHER INFORMATION: Xaa may be Thr, Ala or Ile
<220> FEATURE:
<221> NAME/KEY: VARIANT
<222> LOCATION: (147)..(147)
```

```
<223> OTHER INFORMATION: Xaa may be Arg or Lys
<220> FEATURE:
<221> NAME/KEY: VARIANT
<222> LOCATION: (148)..(148)
<223> OTHER INFORMATION: Xaa may be Arg or Gly

<400> SEQUENCE: 29

Met Gln Ile Pro Gln Ala Pro Trp Pro Val Trp Ala Val Leu Gln
1               5                   10                  15

Leu Gly Trp Arg Pro Gly Trp Phe Leu Asp Ser Pro Asp Arg Pro Trp
                20                  25                  30

Xaa Pro Pro Thr Xaa Ser Pro Ala Leu Leu Val Val Xaa Glu Gly Asp
                35                  40                  45

Xaa Xaa Thr Phe Thr Cys Ser Phe Ser Asn Xaa Ser Glu Ser Phe Val
50                      55                  60

Leu Asn Trp Tyr Arg Xaa Ser Pro Ser Xaa Gln Xaa Asp Lys Leu Ala
65                  70                  75                  80

Ala Phe Pro Glu Asp Arg Xaa Xaa Xaa Gly Xaa Xaa Xaa Arg Phe Xaa
                85                  90                  95

Val Xaa Xaa Leu Pro Xaa Gly Arg Asp Phe Xaa Met Ser Val Val Xaa
        100                 105                 110

Ala Arg Xaa Xaa Asp Ser Gly Thr Tyr Leu Cys Xaa Xaa Ile Xaa Leu
        115                 120                 125

Ala Pro Xaa Xaa Gln Ile Xaa Glu Ser Leu Xaa Xaa Glu Leu Arg Val
130                 135                 140

Xaa Glu Xaa Xaa Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
            275                 280                 285
```